US008992543B2

(12) United States Patent
Yamaguchi et al.

(10) Patent No.: US 8,992,543 B2
(45) Date of Patent: Mar. 31, 2015

(54) TIGHTENING DEVICE FOR BONE FASTENING CABLE

(75) Inventors: Noritoshi Yamaguchi, Osaka (JP); Shinetsu Kudo, Noda (JP); Yoshinori Kohara, Noda (JP); Yasuyuki Hitomi, Kameoka (JP)

(73) Assignees: Alfresa Pharma Corporation, Osaka-Shi, Osaka (JP); Maruho Hatsujyo Kogyo Co., Ltd., Kyoto-Shi, Kyoto (JP)

( * ) Notice: Subject to any disclaimer, the term of this patent is extended or adjusted under 35 U.S.C. 154(b) by 404 days.

(21) Appl. No.: 13/502,870

(22) PCT Filed: Oct. 21, 2010

(86) PCT No.: PCT/JP2010/068578
§ 371 (c)(1),
(2), (4) Date: Jun. 29, 2012

(87) PCT Pub. No.: WO2011/049164
PCT Pub. Date: Apr. 28, 2011

(65) Prior Publication Data
US 2012/0265260 A1    Oct. 18, 2012

(30) Foreign Application Priority Data
Oct. 23, 2009    (JP) .................. 2009-244589

(51) Int. Cl.
*A61B 17/58*    (2006.01)
*A61B 17/60*    (2006.01)
(Continued)

(52) U.S. Cl.
CPC ............. *A61B 17/8869* (2013.01); *A61B 17/82* (2013.01); *A61B 17/8861* (2013.01); *A61B 2019/4815* (2013.01); *A61B 2019/4873* (2013.01)
USPC ............................................ 606/103; 606/74

(58) Field of Classification Search
USPC .................. 606/74, 86 R, 103, 105
See application file for complete search history.

(56) References Cited

U.S. PATENT DOCUMENTS

| 5,312,410 A | 5/1994 | Miller et al. |
| 5,395,374 A | 3/1995 | Miller et al. |

(Continued)

FOREIGN PATENT DOCUMENTS

| JP | 35 12766 | 6/1960 |
| JP | 35-12766 Y1 | 6/1960 |

(Continued)

OTHER PUBLICATIONS

International Search Report of PCT/JP2010/068578 (Dec. 9, 2010).
(Continued)

*Primary Examiner* — Andrew Yang
*Assistant Examiner* — Diana S Jones
(74) *Attorney, Agent, or Firm* — Millen, White, Zelano & Branigan, P.C.

(57) ABSTRACT

A bone-tying cable tightening device is disclosed which makes itself unusable after having been used a predetermined number of times. The device includes a grip portion, a rod-like member, a knot-supporting means at the tip, and a cable-holding means to grip and hold the two arms of a cable, and is provided with a sliding block mounted around the rod-like member and connected to a pulling means, and an operation lever, wherein the cable-holding means includes (a) a longitudinal through groove defined in the upper part of the sliding block, (b) a locking recess which extends at the rear end the through groove, either transversing the cross section of the through groove or containing the cross section of the through groove, and whose width in the cross section thereof widens in the rearward direction, and (c) a backward biased locking member which is provided movably back and forth behind the locking recess on the upper side of the sliding block and so made that its forward movement is blocked when it fits in the locking recess, and wherein the device further includes a pull-releasing means which can be operated to release the one-way detent means for the pulling means, and a release locking means to lock the one-way detent means in a released state after the pull-releasing means has been operated a predetermined number of times.

8 Claims, 16 Drawing Sheets

(51) Int. Cl.
   *A61F 2/00*    (2006.01)
   *A61B 17/82*   (2006.01)
   *A61F 2/30*    (2006.01)
   *A61B 17/88*   (2006.01)
   *A61B 19/00*   (2006.01)

(56) References Cited

U.S. PATENT DOCUMENTS

| | | | |
|---|---|---|---|
| 5,569,253 A | 10/1996 | Farris et al. | |
| 5,928,237 A | 7/1999 | Farris et al. | |
| 6,077,268 A | 6/2000 | Farris et al. | |
| 8,029,513 B2 | 10/2011 | Konno et al. | |
| 2009/0082821 A1* | 3/2009 | Konno et al. | 606/86 A |

FOREIGN PATENT DOCUMENTS

| | | |
|---|---|---|
| JP | 05 317332 | 12/1992 |
| JP | 5-317332 A | 12/1993 |
| JP | 8-504119 A | 5/1996 |
| JP | 9-502112 A | 3/1997 |
| JP | 9-510890 A | 11/1997 |
| JP | 2006-305211 A | 11/2006 |

OTHER PUBLICATIONS

Maruho Hatsujo Kogyo, "Ligating device for bone operation thread," Patent Abstracts of Japan, Publication Date: Dec. 3, 1993; English Abstract of JP-05 317332.

Mizuho Ikakogyo Co. Ltd., "Steel wire tightening device for fractured bones," Patent Abstracts of Japan, Publication Date: Jun. 10, 1960; English Abstract of JP-35-12766.

* cited by examiner

TIGHTENING DEVICE FOR BONE FASTENING CABLE

TECHNICAL FIELD

The present invention relates to a bone-tying cable tightening device for use in bone surgeries, such as those for treatment of bone fracture, repositioning and fixation of bones or the like in order to tighten a bone-tying cable used to firmly tie bones in an affected part of the body together and keep holding them, with a strength of force required to keep holding them, so as to allow them to fuse and unite with each other.

BACKGROUND ART

For fixation of bones (i.e., fusion and unification of bones) in bone surgeries, such as repositioning of bones after spinal fractures, bone grafting, and the like, the bones must, in order for their fixation, be kept tightly held together, so that they may not be displaced before their fusion is completed. Recently, for the purpose of achieving such holding, cables made of high-strength synthetic fibers, like high molecular weight polyethylene (referred to as "bone-tying cables" in the present invention), have been used.

In a surgery employing bone-tying cables, as FIG. 1 schematically illustrates a typical manner of tying with an above-mentioned cable which is made of synthetic fibers, such a procedure is followed that bones to be held together (shown in the form of round bars) are first tied with a loop of the bone-tying cable (together with a rod, a hook or the like to serve as a splint, if necessary) (FIGS. 1(a)-(f)), and then, (1) while the knot (provisional knot) shown in FIG. 1(f) is supported, the two arms of the cable extending from it are held together and pulled tightly so that the size of the loop is reduced and the bones thereby are fastened to each other, and, after the tension of the loop has been increased up to a required level, then keeping that condition, the knot is immobilized with, e.g., an adhesive or an attachment, or (2) a provisional knot is formed starting from the condition as depicted in FIG. 1(g) by pulling the two arms in the directions indicated with the arrowheads, and, the two arms of the cable extending therefrom are then pulled firmly in both lateral directions so that the size of the loop is reduced and the bones thereby are fastened to each other, and, after the tension of the loop has been increased up to a required level, then keeping the tension, the knot is immobilized by means of additional knots or an adhesive or the like, as required to prevent it from slipping.

It is required that the above fastening with the bone-tying cable must create a strong tension (e.g., 5-10 kgf) in the cable which forms the loop. In order to overcome the frictional force between the fibers of the cable within the provisional knot, thereby causing cable portions to slip with one another and thus reducing the size of the loop to achieve such a strong tension in it, the two arms extending from the provisional knot must be pulled with a greater tension. A device is sold as a product to enables this, which is a "bone-tying cable tightening device" described in Patent No. 3721189 (Patent Literature 1), [Tighting Gun [MAH], mftd. by Alfresa Pharma Corporation].

While the above device can be used repeatedly for an extended period of time, through repeated washing and sterilization performed after each use, it requires regular maintenance by its producer, since it is a device used in a surgery. Thus, the products delivered to each medical facility must be kept under control, each by separately setting the timing for maintenance. For maintenance, each device must be recovered from the medical facility, and after its disassembling, examination, fine adjustment, washing and the like, be returned to the medical facility which owns it. The process of maintenance, including a series of actions like schedule management, recovery, examination, and adjustment, as well as returning of the device, requires a lot of manpower and its cost-efficiency is very low. Furthermore, because of its presumed repetitive and extended use, this type of device is made, almost entirely, of metal in order that it should stand through such use, and, in consequence, is costly to produce. Thus it is difficult to curtail the total cost per device, including the cost for its maintenance. Further, it also is a trouble that, since it is impossible for its producer to directly know in what manner, e.g., how often, a device has been used at each facility, it is not an easy matter to determine whether the frequency of maintenance set for each device is appropriate or not. Furthermore, the device has another drawback that, as it is made, almost entirely, of metal and therefore is heavy, some operators feel its weight as a burden.

PRIOR ART LITERATURES

Patent Literatures

[Patent Literature 1] JP Patent No. 3721189

SUMMARY OF INVENTION

Technical Problem

The cost for production of the above device can be greatly reduced if its parts, except those which require especially high strength, are made of plastics, because in that case most of its parts are to be replaced with plastic ones. Further, in such a case, it would be beneficial that since the device would become less heavy, it would be handled by the operator more easily. However, the device is washed and heat sterilized each time after it is used in an operation. Thus, a device in which a number of plastic parts are used is less durable than conventional one, which consists almost entirely of metal parts. Therefore, it must be a rule that such a device should be disposed of, and should not used again, after it has been used a certain number of times. If it is made a rule that, setting a maximum number of times up to which the device may be used safely and reliably without maintenance, the device should be discarded at the medical facility after having been used such number of times, no cost for its maintenance would arise, and therefore the total cost of the device would be further reduced. In that case, moreover, as the device is disposable, an effect of mass production would work, which would still further reduce the production cost per device.

However, just ruling of such a maximum allowable times of use would not guarantee that the rule be strictly abided by at medical facilities, but it could happen that the rule would be overlooked, with devices significantly exceeding the maximum allowable times of use being put to use. In such a case, it is impossible to guarantee the reliability in function and safety of the devices, thereby giving rise to a grave problem.

Against the above background, the objective of the present invention is to provide an above-mentioned bone-tying cable tightening device which is provided with a function that guarantees to make the device no longer usable once it has been used a predetermined number of times.

Means to Solve the Problem

The present inventors, focusing attention on the operation of releasing a pull, which is necessarily involved once following each use of the above-mentioned current device, completed a device which is a type of above-mentioned device and is characterized that it makes itself unusable when the operation of releasing a pull has been performed a predetermined number of times. Thus the present invention provides what follows.

1. A bone-tying cable tightening device for firmly tying up objects to be tied, by pulling the two arms which extend from the knot of a cable which ties the objects to be tied, comprising a grip portion to be held with a hand, a rod-like member which extends forward from the grip portion, a knot-supporting means provided at the tip of the rod-like member to support the knot when the two arms are pulled, a sliding block mounted around the rod-like member in a longitudinally slidable fashion, which sliding block is provided with a cable-holding means to grip and hold the two arms together, a pulling means installed in the grip portion to pull the sliding block, which pulling means is connected to the sliding block via a tension transmitter means, an operation lever provided in the grip portion to drive the pulling means, wherein the knot-supporting means is of a structure which defines, above the rod-like member, (1) supporting faces on both sides thereof on which the two arms can be hooked away from each other and laterally relative to the longitudinal axis of the rod-like member, and/or (2) a slit or bore through which the two arms can be passed, and wherein the cable-holding means provided to the sliding block comprises (a) a longitudinal through groove defined in the upper part of the sliding block, (b) a locking recess which extends at the rear end of the through groove, either transversing the cross section of the through groove or containing the cross section of the through groove along the central axis thereof, and whose width, in the cross section thereof, widens in the rearward direction, (c) a backward biased locking member about which the two arms are to be wound, and which is provided movably back and forth behind the locking recess on the upper side of the sliding block and is so made that the forward movement thereof is blocked when it proceeds in the locking recess and abuts, with the side faces thereof, on the same, and wherein, the pulling means includes a one-way detent means which acts to prevent returning of the pulling means from the position to which the pulling means has been driven to the position at which the pulling means rested before being driven, the device is provided with a pull-releasing means which releases the one-way detent means to allow the pulling means to return from the position up to which the pulling means has been driven to the position at which the pulling means rests before driven, which pull-releasing means is so configured as to allow a releasing operation from outside of the device, and wherein the device is provided with a release locking means which locks the one-way detent means in a released state once the pull-releasing means has been operated the predetermined number of times.

2. The bone-tying cable tightening device according to 1 above, wherein the release locking means is advanced stepwise, by each operation of the pull-releasing means, from a predetermined initial position at which the release locking means does not prevent the action of the one-way detent means toward a predetermined final position at which the release locking means locks the one-way detent means in a released state, and wherein the release locking means is so configured as to reach the predetermined final position and lock the one-way detent means in the released state after the pull-releasing means has been operated the predetermined number of times.

3. The devise according to 1 or 2 above, wherein the pulling means includes a first ratchet wheel which is advanced stepwise in one direction by the operation of the operation lever, wherein the one-way detent means is a one-way detent which engages the first ratchet wheel.

4. The device according one of 1 to 3 above, wherein the release locking means includes a second ratchet wheel which is advanced stepwise in one direction by the operation of the pull-releasing means and a stopper which is advanced toward the final position by the advance of the second ratchet wheel, wherein the stopper is so configured as to abut, at the final position, on the one-way detent means or a member which is interlocked therewith to prevent the motion thereof, and thereby to lock the one-way detent means in a released state.

Effect of the Invention

According to the present invention as defined above, the number of times the device has been used is counted based on the operation of the pull-releasing means, and when the number of times of use has reached a predetermined number, the pull is released and locked in the state. Therefore, the device then can no longer be used after it has been used the predetermined number of times. The device according to the present invention thus guarantees itself to be disposed of after used the predetermined times at medical facilities. Therefore, as it is enough for the device to have such an extent of durability that guarantees with certainty its use for the predetermined number of times, it becomes possible to replace most of its parts, which are conventionally made of metal, with those made of plastic, thereby reducing its production cost, and also greatly reducing its weight. Further, since the device will be discarded after having been used the predetermined number of times, and a fresh device will be used thereafter, the maintenance, which has been performed with the conventional devices, becomes no longer necessary at all, thus also eliminating the costs relating thereto. Furthermore, as the device is of a disposable type, it is possible to greatly reduce the cost per device also by the effect of mass production.

DESCRIPTION OF EMBODIMENTS

Figure 1:
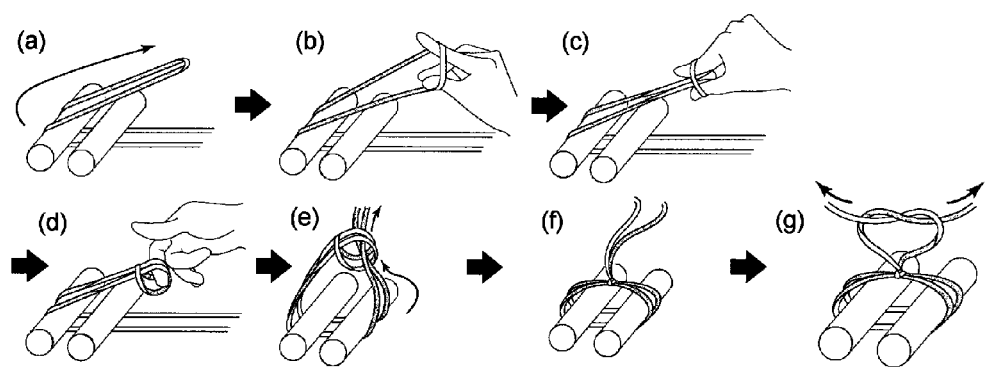
FIG. 1 is a schematic diagram showing the manner how to loop a bone-tying cable around bones and to form a provisional knot to it.

The bone-tying cable tightening device according to the present invention may take a variety of specific forms as mentioned below.

1. A bone-tying cable tightening device for firmly tying up objects to be tied, by pulling the two arms which extend from the knot of a cable which ties the objects to be tied, comprising a grip portion to be held with a hand, a rod-like member which extends forward from the grip portion, a knot-supporting means provided at the tip of the rod-like member to support the knot when the two arms are pulled, a sliding block mounted around the rod-like member in a longitudinally slidable fashion, which sliding block is provided with a cable-holding means to grip and hold the two arms together, a pulling means installed in the grip portion to pull the sliding block, which pulling means is connected to the sliding block via a tension transmitter means, an operation lever provided in the grip portion to drive the pulling means, wherein the knot-supporting means is of a structure which defines, above the rod-like member, (1) supporting faces on both sides thereof on which the two arms can be hooked away from each other and laterally relative to the longitudinal axis of the rod-like member, and/or (2) a slit or bore through which the two arms can be passed, and wherein the cable-holding means provided to the sliding block comprises (a) a longitudinal through groove defined in the upper part of the sliding block, (b) a locking recess which extends at the rear end of the through groove, either transversing the cross section of the through groove or containing the cross section of the through groove along the central axis thereof, and whose width, in the cross section thereof, widens in the rearward direction, (c) a backward biased locking member about which the two arms are to be wound, and which is provided movably back and forth behind the locking recess on the upper side of the sliding block and is so made that the forward movement thereof is blocked when it proceeds in the locking recess and abuts, with the side faces thereof, on the same, and wherein, the pulling means includes a one-way detent means which acts to prevent returning of the pulling means from the position to which the pulling means has been driven to the position at which the pulling means rested before being driven, the device is provided with a pull-releasing means which releases the one-way detent means to allow the pulling means to return from the position up to which the pulling means has been driven to the position at which the pulling means rests before driven, which pull-releasing means is so configured as to allow a releasing operation from outside of the device, and wherein the device is provided with a release locking means which locks the one-way detent means in a released state once the pull-releasing means has been operated the predetermined number of times.

2. The bone-tying cable tightening device according to 1 above, wherein the release locking means is advanced stepwise, by each operation of the pull-releasing means, from a predetermined initial position at which the release locking means does not prevent the action of the one-way detent means toward a predetermined final position at which the release locking means locks the one-way detent means in a released state, and wherein the release locking means is so configured as to reach the predetermined final position and lock the one-way detent means in the released state after the pull-releasing means has been operated the predetermined number of times.

3. The devise according to 1 or 2 above, wherein the pulling means includes a first ratchet wheel which is advanced stepwise in one direction by the operation of the operation lever, wherein the one-way detent means is a one-way detent which engages the first ratchet wheel.

4. The device according one of 1 to 3 above, wherein the release locking means includes a second ratchet wheel which is advanced stepwise in one direction by the operation of the pull-releasing means and a stopper which is advanced toward the final position by the advance of the second ratchet wheel, wherein the stopper is so configured as to abut, at the final position, on the one-way detent means or a member which is interlocked therewith to prevent the motion thereof, and thereby to lock the one-way detent means in a released state.

5. The bone-tying cable tightening device according to one of 1 to 4 above, wherein the locking recess extends containing the cross section of the through groove along the central axis thereof.

6. The bone-tying cable tightening device according to 5 above, wherein the locking member is attached to an arm which is installed, pivotably about a vertical axis, on the sliding block and on the same side as the knot-supporting means relative to the rod-like member.

7. The bone-tying cable tightening device according to 6 above, wherein the locking recess defines in the edge thereof an indentation which can accommodate the arm as the locking member fits in the locking recess.

8. The bone-tying cable tightening device according to 6 above, wherein the arm has a contour which evades the edge of the locking recess so that the arm may avoid interference with the edge of the locking recess as the locking member fits in the locking recess.

9. The bone-tying cable tightening device according to one of 6 to 8 above, wherein the arm is journaled on the sliding block.

10. The bone-tying cable tightening device according to 9 above, wherein the backward bias for the locking member is given by a spring installed around the pivotal shaft of the arm journaled on the sliding block.

11. The bone-tying cable tightening device according to 5 above, wherein the locking member is installed at the tips of the second arms of a five-link chain mechanism which consists of a pair of first lateral arms of equal length which are installed, on the same side as the knot-supporting means relative to the rod-like member, pivotably about vertical axes on both lateral sides of the sliding block and extending diagonally in lateral directions, respectively, and a pair of second lateral arms of equal length which are attached, pivotably about vertical axes, to one or the other of the pair of first lateral arms at the tips thereof, and extends diagonally in inward directions therefrom, respectively, the tips of the pair of second arms being connected pivotably with each other about a vertical axis.

12. The bone-tying cable tightening device according to 11 above, wherein the pair of first arms are journaled on the sliding block.

13. The bone-tying cable tightening device according to 12 above, wherein the backward bias for the locking member is given by a spring installed around at least one of the pivotal shafts of the pair of first arms journaled on the sliding block.

14. The bone-tying cable tightening device according to 5 above, wherein the locking member is installed on a sliding member which is mounted on, and slidably back and forth relative to, the sliding block.

15. The bone-tying cable tightening device according to 14 above, wherein the sliding member slides along a sliding guide formed in the sliding block and to which part of the sliding member fits.

16. The bone-tying cable tightening device according to 15 above, wherein the backward bias for the locking member is given by a spring installed in the sliding guide in association with the sliding member.

17. The bone-tying cable tightening device according to 4 above, wherein the locking recess extends transversing the cross section of the through groove.

18. The bone-tying cable tightening device according to 17 above, wherein the locking member is mounted on an arm which is installed, pivotably about a horizontal axis, on a lateral side of the sliding block.

19. The bone-tying cable tightening device according to 18 above, wherein the arm extends generally in the upward direction from a lateral side of the sliding block, and the locking member extends from the tip of the arm, in the rear of the locking recess and in parallel to the same.

20. The bone-tying cable tightening device according to 18 above, wherein the arm extends generally in the upward direction separately from the both lateral sides of the sliding block, respectively, and then inward above the sliding block to unite into one body, and again generally in the upward direction, and at the tip of the arm the locking member is attached.

21. The bone-tying cable tightening device according to one of 18 to 20 above, wherein the arm is journaled on the sliding block.

22. The bone-tying cable tightening device according to 21 above, wherein the backward bias for the locking member is given by a spring installed around the pivotal shaft of the arm journaled on the sliding block.

23. The bone-tying cable tightening device according to 17 above, wherein the locking member is installed on a sliding member which is mounted on the sliding block, slidably back and forth relative thereto.

24. The bone-tying cable tightening device according to 23 above, wherein the sliding member slides along a sliding guide which is formed in the sliding block and to which part of the sliding member fits.

25. The bone-tying cable tightening device according to 24 above, wherein the backward bias for the locking member is given by a spring installed in the sliding guide in association with the sliding member.

26. The bone-tying cable tightening device according to one of 1 to 25 above, wherein the width of the locking recess in the cross section thereof widens in a V-shaped fashion in the rearward direction.

27. The bone-tying cable tightening device according to one of 1 to 25 above, wherein the width of the locking recess in the cross section thereof widens in a circular arc-like fashion in the rearward direction.

In the present invention, there is no particular limitation as to the shape and size of the grip portion insofar as it is easy to grip and handle. The rod-like member extending from the grip portion may be fixed to the grip portion, or it may be attached in such a manner that it can retreat by sliding when pulled with a force beyond a predetermined strength. There is no particular limitation as to the length and thickness of the rod-like member. As to its length, it is enough that the rod-like member reserves a space for the sliding block to retreat by at least about several centimeters. And as to its thickness, it is enough that the rod-like member endures a longitudinal compressive force of several dozen kgf. The shape of its cross section may also be as desired as long as it allows sliding motion of the sliding block. It is convenient to provide the rod-like member with a cross section of, for example, rectangular.

The knot-supporting means is a means for supporting a provisional knot against the tension which pulls rearward the two arms of the bone-tying cable extending from the provisional knot. The knot-supporting means may be (1) of a type according to which the provisional knot is placed in the middle of the knot-supporting means and then the two arms of the cable, which are separated in both lateral directions, are pulled backward, or (2) of a type which has a bore or slit of a width that allows to pass and pull the two arms of the cable backward through it (but not allowing the provisional knot of the cable to pass through it), or further (3) of a type in which the former two types are combined together. Specifically, a knot-supporting means of type (1) may be, for example, in the form of a projection, or a pair of projections placed adjacent to each other and in bilaterally symmetrical arrangement, at the tip of the rod-like member, or may be provided as a portion which is formed by bending the tip of the rod-like member upward. In these cases, since the arms of the cable are drawn along the side faces of it, the knot-supporting member preferably has smooth surfaces at least on its side faces which support the cable, in order to avoid excess friction. Further, it is preferred that the knot-supporting member has on each of its side faces a recessed area (e.g., a recessed area conforming to a saddleback surface) in order to prevent the two arms of the cable from slipping off upward from the knot-supporting means as the two arms of the cable are pulled along the side faces of the knot-supporting means. Further, specific examples of type (2) include a pair of projections on the rod-like member so arranged as to define a slit between them (of whatever longitudinal depth) which allows the cable to be passed through in the backward direction, and a projection having a through bore, as well as a cylindrical or an annular structure defining a bore facing in the longitudinal direction. Specific examples of a type in which types (1) and (2) are combined together include a pair of projections of type (1) the space between which is made in the form of a slit of type (2), as well as a single projection of type (1) which defines a through bore in the longitudinal direction.

As the through groove defined in the sliding block is for receiving sideways the two arms of the bone-tying cable pulled in a bundle, what is required for the through groove is that it has a sufficient width and depth to let the cable's two arms pass through within itself. What is required for the locking recess is that it blocks the forward movement of the locking member that has fit in it, by abutting with its side faces on the side faces of the locking member. Therefore, the shape and size of it may be determined to meet this purpose as desired in accordance with the size of the locking member. Though it is convenient to give the locking recess a V-shaped cross section, it is also be possible to make it in the form of a groove having a round cross section, e.g., arc-like one, in which case the dimensions of the locking recess may be determined so that the two cable's arms wound about the locking member may be clamped between the locking member and sloping areas in the arc-like cross section on both sides of the locking recess. Regardless of whether it is V-shaped or of arc-like in its cross section, the slope of the surfaces between which the cable is clamped and locked is preferably not less than 45 degrees, more preferably not less than 55 degrees, still more preferably not less than 60 degrees, relative to a plane perpendicular to the direction in which the cable is pulled. In addition, the side faces of the locking member or the surface of the locking recess, or both of them, may have been subjected to a surface roughening process by, e.g., giving fine notches in them to create uneven surfaces, in order to increase their friction with the cable and thereby to achieve securer locking.

The locking recess may extend containing in itself the cross section of, and along its central axis of, the through groove in the sliding block, or it may extend transversing the cross section of the through groove. In the former case, the basal portion of the locking recess is penetrated by the cross section of the through groove, and therefore the locking recess includes only the faces left on both sides, the faces which take part in engagement. In the case where the locking recess is given so that it transverses the through groove, the locking recess, though divided around its center by the cross section of the through groove, holds its intact shape in the remaining portion.

The locking member is oriented in parallel to the direction in which the locking recess extends. The locking member is attached, on the same side as the knot-supporting means relative to the rod-like member, to an arm which is installed, e.g., pivotably about a vertical axis, on the sliding block, and thus can come into and out of the locking recess from behind, moving along a circular orbit in a horizontal plane according to the swing of the arm. In this case, the arm may be given, on the side opposing to the edge of the locking recess, a contour having a recess into which the edge of the locking recess is received, by, e.g., bending the arm into the form of a hook, in order to avoid interference of the arm with the edge of the locking recess. Alternatively, an indentation may be given to the edge of the locking groove by removing part of it so that the arm can be received therein.

The above-mentioned arm may be journaled on the sliding block via a shaft member pivotably attached to the sliding block. The backward bias for the locking member (therefore, for the arm) may be given by placing a spring around the shaft member within the sliding block.

In an arrangement which substitutes for the above single-arm arrangement, the locking member may be installed at the tip of a five-link chain which is formed including the sliding block. Namely, the locking member may be installed at the tips of the second arms of a five-link chain mechanism which consists of a pair of first lateral arms of equal length which are installed, on the same side as the knot-supporting means relative to the rod-like member, pivotably about vertical axes generally symmetrically on both lateral sides of the sliding block and extending diagonally in lateral directions, respectively, and a pair of second lateral arms of equal length which are symmetrically attached, pivotably about vertical axes, to one or the other of the pair of first lateral arms at the tips thereof, and extends diagonally in inward directions therefrom, respectively, the tips of the pair of second arms being connected pivotably with each other about a vertical axis. This arrangement is that of a pantograph, according to which the locking member can come to fit in the locking recess moving along a straight line, not an arc. In this arrangement, the proximal ends of the pair of first arms may be journaled on the sliding block via corresponding shaft members pivotably installed in the sliding block, and the backward bias for the locking member may be given by a spring or springs installed around one or the both of the shaft members in the sliding block.

Instead of these single-arm and multiple-arms arrangements, it is also possible to employ a sliding member, e.g. a plate-like member, which is mounted on the sliding block, slidably back and forth relative to it, on which the locking member is installed, and which is biased backward by a spring. For the back-and-forth sliding of the sliding member, a guide (sliding guide) may be provided on the sliding block. A sliding guide may, for example, consist of guide bores which receives, slidably in the longitudinal direction, front and rear parts of the sliding member, respectively; or of a pair of projections, each having an L-shaped cross section, which slidably hold between them the sliding member on both sides thereof, and projections provided in front of and behind the sliding member, respectively, to confine its longitudinal motion within a predetermined range. A spring which biases the sliding member (therefore the locking member) backward may, for example, be installed within one of the above-mentioned guide bores, or between one of the above-mentioned projections (e.g., the projection in the rear) and the sliding member.

In the case where the locking recess extends in the horizontal direction transversing the cross section of the longitudinal through groove, the locking member which is to fit in the locking recess also is positioned horizontally oriented accordingly. In this case, too, the back-and-forth motion of the locking member may be allowed either by placing it on an arm pivotably installed on the sliding block, or by placing it on a sliding member slidably installed on the sliding block. Specifically, for example, the locking member may be attached, in the rear of and in parallel to the locking recess, to the tip of an arm which is installed pivotably about a horizontal axis on a lateral side of the sliding block, or it may be attached, in the rear of and in parallel to the locking recess, to the tip of an arm which, after first extending separately from the both lateral sides of the sliding block, generally in the upward direction in a vertical plain, respectively, extends inward, above the sliding block, to unite into one body in the middle, and again extends generally in the upward direction. Employment of one of such arrangements allows the locking member to fit in the locking recess, moving in the longitudinal direction in an orbit, which is either circular or straight. A method for biasing the locking member backward may be the same as described above as to a vertical locking member.

There is no particular limitation regarding the specific structure of the grip portion. The grip portion is provided with an operation lever and a pulling means which is driven by pulling of the operation lever. The pulling means may comprise a pull cable (i.e., the tension transmitter means) winding means, such as, for example, a rotary drum which is rotated stepwise in a fixed direction (directly, or via a separate convenient mechanism, such as gears) by a ratchet mechanism which works in association with the pulling of the operation lever. In that case, the pull cable may be secured at one end to the pull cable winding means, and at the other end to the rear face of the sliding block. Repeated pull of the operation lever rotates the cable winding means, which then pulls the pull cable backward, causing the sliding block thus pulled to slide backward on the rod-like member.

The rod-like member may be supported by the grip portion in such fashion that it by itself is slidable in the proximal direction toward the surgeon. In that case, an arrangement may be applicable in which the proximal end of the rod-like member rests on one end of a spring (e.g., a coil spring) installed in the grip portion, so that as the sliding block is pulled backward, the rod-like member, which is also pulled backward via the bone-tying cable held by the sliding block, may start to retreat just when the amount of the pulling force goes up beyond a predetermined value. By employing that arrangement, the device is made so that it can inform the surgeon just after the tension has reached the predetermined value. The amount of tension at which the rod-like member starts to retreat may be set as desired, by having compressed the spring which lies abutting on the rear end of the rod-like member to a position at which the repulsive force generated within the spring equals the predetermined tension. To do so, for example, the portion of the grip member in which the spring is installed may be built so that the spring may be fit within a framework which can compress it to limit its maximum allowable length, with the maximum length of the framework being made adjustable by a screw mechanism.

The grip portion is provided with a one-way detent means, which prevents returning of the pulling means, so that it may not, while it is pulling the sliding block via the tension transmitter means, turn back to a position (the term "position" embracing angular measure) it took before pulling. In the case where the pulling means includes a ratchet mechanism as a component, a preferred but nonlimiting example of a one-way detent means is a one-way detent which engages the teeth of the ratchet wheel.

The grip portion is provided with a pull-releasing means in order that the pulling means can be returned to its pre-driven position after it has completed the pulling of the sliding block. In the case where the pulling means includes a ratchet mechanism as a component, the pull-releasing means may be any one of convenient mechanisms as desired which, for example, acts to disengage the tip of the one-way detent engaging the teeth of the ratchet wheel. Such a mechanism can readily be configured by, for example, installing a release lever on the outside of the grip portion, and positioning the one-way detent inside the grip portion on a pivotal shaft for the release lever, or on a basal plate which moves in association with the pivotal shaft, so that the tip of the one-way detent disengages the teeth of the ratchet wheel only when the release lever is activated.

The device of the present invention is provided with a release locking means, which acts to lock the one-way detent means at its released position once the pull-releasing means has been activated a predetermined number of times, so that the pulling means may no longer work. This may be achieved by, for example, installing a member which is advanced stepwise each time when the pull-releasing means is activated, until it reaches a predetermined position where it abuts on the pull-releasing means, or on the one-way detent means moving in association therewith, or on any other convenient member as desired, to restrict their further movement, consequently locking the one-way detent means at the released state. More specifically, this may be achieved by, for example, installing a ratchet mechanism including a ratchet wheel, a feed pawl which is moved in association with the pull-releasing means (e.g., including the releasing lever) to advance the ratchet wheel, and a one-way detent in the grip portion, so that the ratchet wheel may be advanced stepwise when the pull-releasing means is activated, and installing a proper stopper (a projection, etc.) on the ratchet wheel (or on other convenient member which moves in association with the advancement of the ratchet wheel), so that once the pull-releasing means has been activated a predetermined number of times, the stopper abuts on the pull-releasing means (or on the one-way detent means released thereby, or on any other convenient member moving in association with them) to prevent further movement of such members, thereby locking the one-way detent means at the released state.

Further, the grip portion may be provided with a locking means for preventing an inadvertent activation of the pull-releasing means. A locking mans may, for example, be a member which can be switched between a position where it abuts on, and thereby hinders the movement of, the releasing lever and a position where it does not hinder the movement, and sifting of such a member between those positions may be allowed by, for example, placing it in a manner that it can be slid within a predetermined range.

The device according to the present invention can prevent, by its own mechanism, itself from being used exceeding a predetermined number of times. Therefore, it is not necessary with the device of the present invention to expect such a case where it be used repeatedly for an extended period of time, but it is enough that the device has a level of durability that withstands while being used a predetermined number of times (and washing and heat sterilization performed while it is used). That permits that most of its parts, other than gears, a ratchet mechanism, or a spring, be made of plastics. Preferred plastics are, for example, heat-resistant, high-strength engineering plastics.

EXAMPLES

While the present invention is described below in further detail with reference to an example, it is not intended that the present invention be limited to the examples.

Example 1

Figure 2:
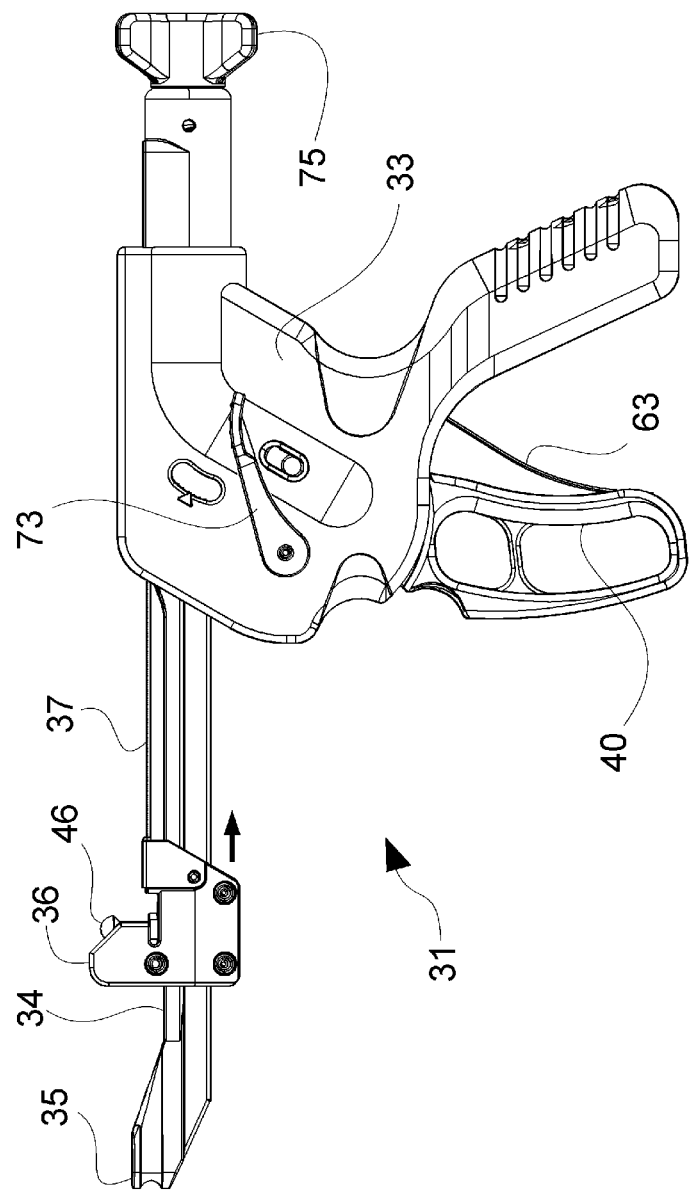
FIG. 2 illustrates a side view of the device of Example 1 of the present invention.
Figure 3:
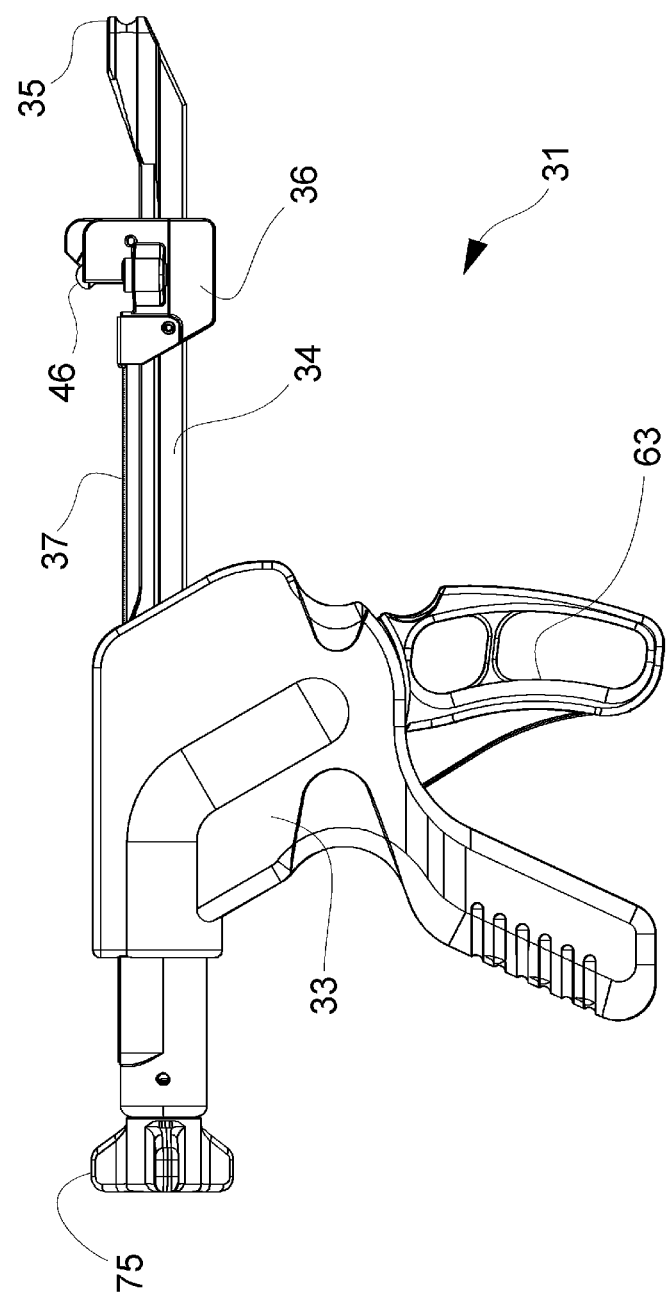
FIG. 3 illustrates a side view of the device of Example 1 of the present invention seen from the opposite side to that shown in FIG. 2.
Figure 4:
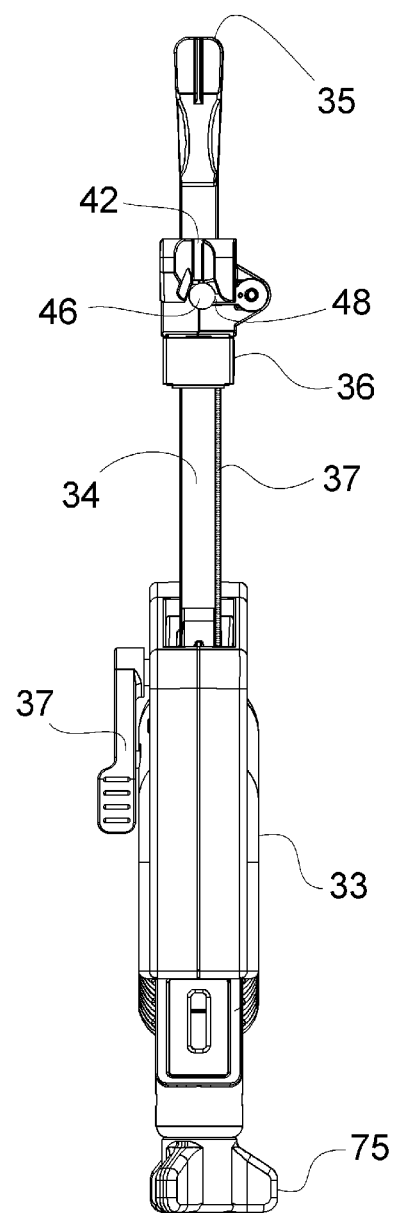
FIG. 4 illustrates a plan view of the device of Example 1 of the present invention.
Figure 5:
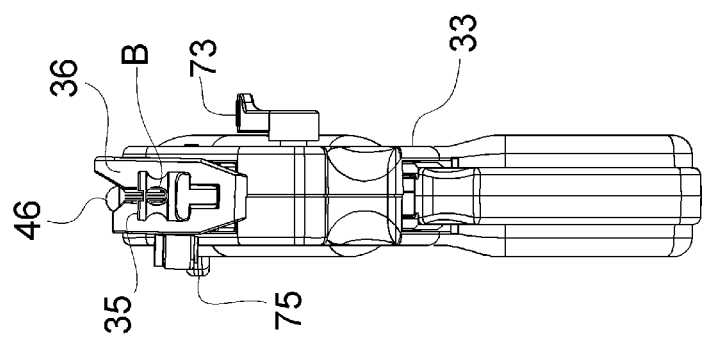
FIG. 5 illustrates a front view of the device of Example 1 of the present invention.
Figure 6:
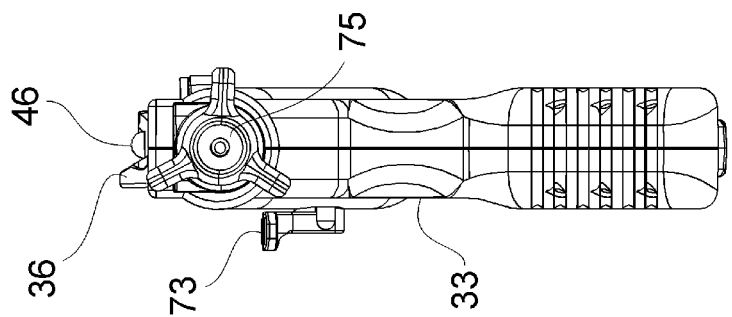
FIG. 6 illustrates a back view of the device of Example 1 of the present invention.

FIG. 2 illustrates a side view of the bone-tying cable tightening device 31 of Example 1 of the present invention, FIG. 3 a side view seen from the opposite side to that seen in FIG. 2, FIG. 4 a plan view, FIG. 5 a front view, and FIG. 6 a back view. In these figures, indicated with the reference number 33 is a grip portion, within which a pulling means and other mechanisms, entirely or partly, are housed, and from the front side of which a rod-like member 34 extends.

Though the device will take a variety of postures in actual use of it, each direction, i.e., the upward, downward, leftward, rightward, forward or backward direction, is defined in these figures, for convenience of description as well as understanding of its structure, with the device being held so that the longitudinal direction of the rod-like member 34 extends horizontally, its tip orienting in the forward direction, and the plane of symmetry of the grip portion 33 (which is bilaterally symmetrical as a whole) being held vertical.

The rod-like member 34 is supported by the grip portion 33 in a backward slidable fashion, but as will be mentioned later, stays in the position as shown in the figure by being strongly biased from behind. At its tip, the rod-like member 34 is provided with a knot-supporting means 35 consisting of an upward-projecting symmetrical portion. The knot-supporting means 35 has smooth side faces, which is recessed in their central area, and serves to support a provisional knot when a bone-tying cable is being tightened. In this example, the know-supporting means 35 also has a longitudinal through bore B in its central area.

Around the rod-like member 34 is slidably fit a sliding block 36, and to the rear part of the sliding block is secured an end of a pull cable 37, which extends from the front face of the grip portion 33. The other end of the pull cable 37 is secured to a rotary drum (not seen in the figure) provided inside the grip portion 33, and the rotary drum is configured so that it may be rotated stepwise only in a fixed direction, by a ratchet mechanism which is caused to act by an operation lever 40 in the shape of a trigger extending from the grip portion 33. Thus, the pull cable 37, which is secured at one end to the rotary drum, is rotated by a constant amount by each pull of the operation lever 40, and thus is pulled backward by the rotary drum which rotates by an amount corresponding to the number of the pull of the operation lever 40, thereby in turn pulling backward the sliding block 36 to which an end of it is secured.

The sliding block 36 defines in its upper part a longitudinal through groove 42 (see FIGS. 4 and 7), and the through groove 42 defines, in its rear edges on both sides, a locking recess 44 (see FIGS. 7 and 10) whose width in the cross section widens in a V-shaped fashion in the rearward direction. In the rear of the locking recess 44, there is placed a locking member 46 in a shape of a bar which is thicker than the width of the through groove 42 and thinner than the locking recess 44. The surface of the locking member 46 is roughened by giving it axial fine notches.

Figure 7:
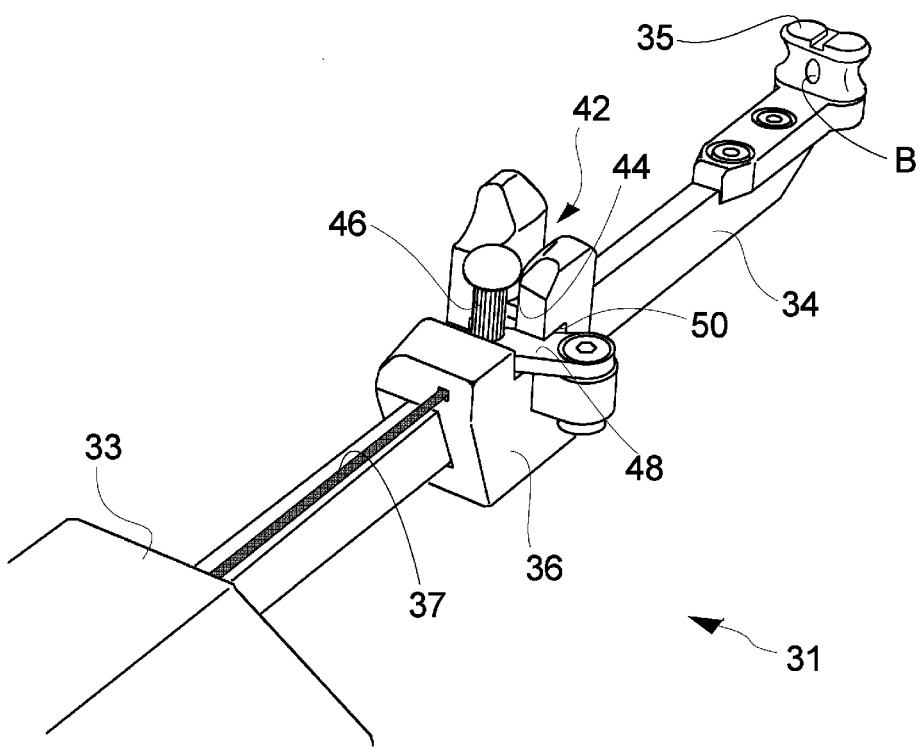
FIG. 7 illustrates an enlarged partial view of the device of Example 1 of the present invention, seen obliquely from behind. The shape of the knot holding means, however, is partly modified.

FIG. 7 (the shape of the knot-supporting means partly modified) illustrates a typical configuration of the sliding block 36 and the locking member associated therewith. The locking member 46 is fixed at its base to one end of an arm 48. The arm 48 is journaled at the other end on the sliding block 36 in such a manner that it can pivot in a horizontal plane about a vertical axis, and, further, is biased backward in such a manner that the locking member 46 is moved away from the locking recess 44, by means of a spring installed around a shaft on which the arm is journaled (not seen in the figures, shielded within the sliding block). Further, the sliding block 36 defines an indentation 50 on an edge of the locking recess to avoid interference between the edge and the arm 48 as the arm moves forward into the locking recess 44. Thus, the locking member 46, though usually positioned in the rearward of the locking recess 44 because of the bias given by the spring, can be fit in the locking recess 44 when an external force in the forward direction is applied to it.

Figure 8:
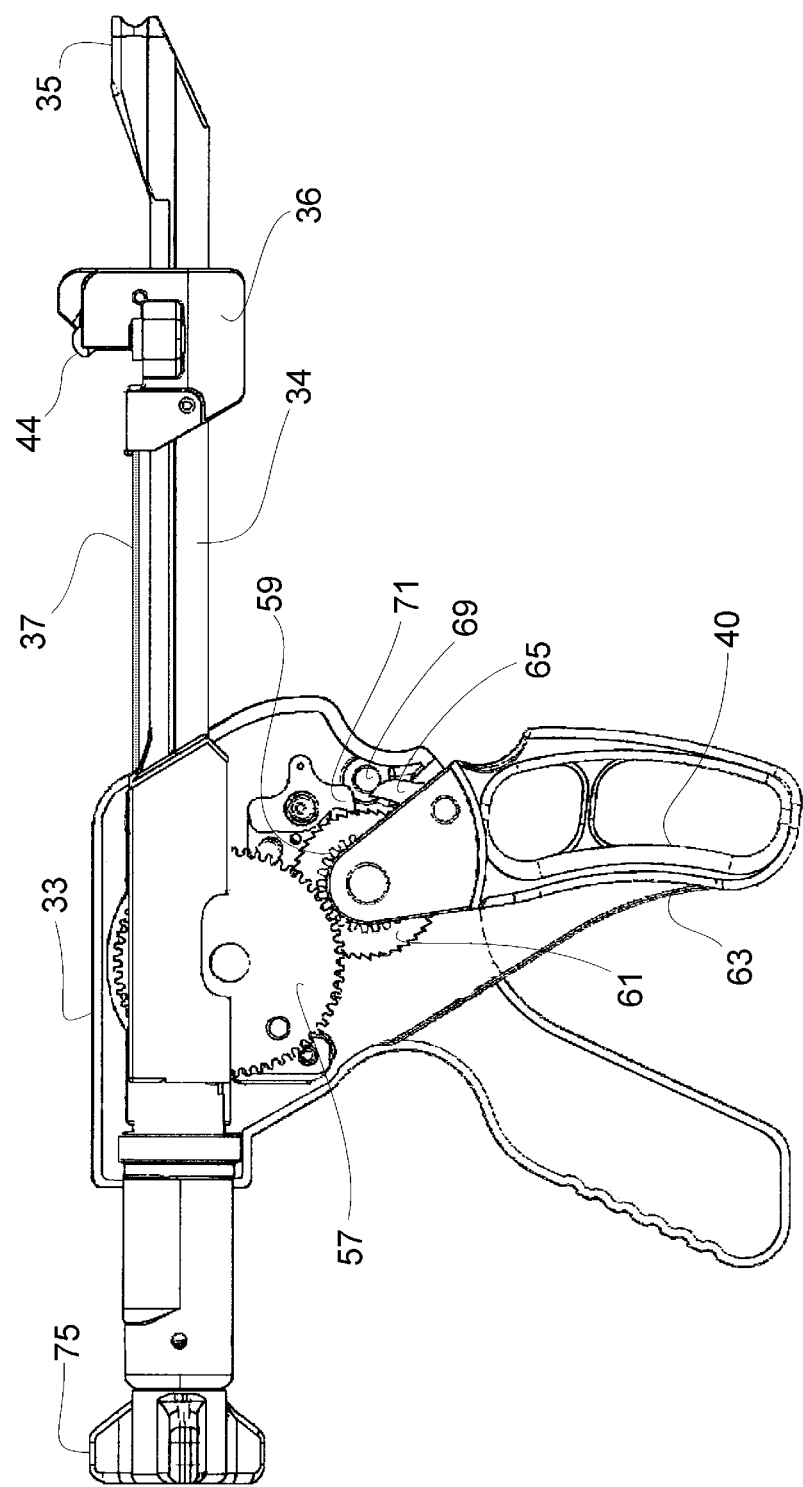
FIG. 8 illustrates a side view of the grip portion of the device of Example 1 of the present invention, with part of the housing on the front side of the drawing removed.

FIG. 8 illustrates a side view of the grip portion of the device, with the front side of the grip portion 33 in the drawing is removed, showing a general internal structure of the grip portion of the device. The pull cable 37 is secured at its rear end to the rotary drum and wound along the drum surface. In the figure, the rotary drum is fixed on the backside of a gear 57, which is coaxially united into a body with the drum surface, and therefore is not seen. The gear 57 is meshed with another gear 59 of a smaller diameter. The gear 59 is united into a body with a coaxial ratchet wheel 61. To the operation lever 40, which is attached coaxially with the ratchet wheel 61, is secured, near its lower end, the lower end of a leaf spring 63, and the upper end of the leaf spring 63 is secured on the housing of the grip portion 33, with the operation lever 40 being biased forward by it.

Figure 9:
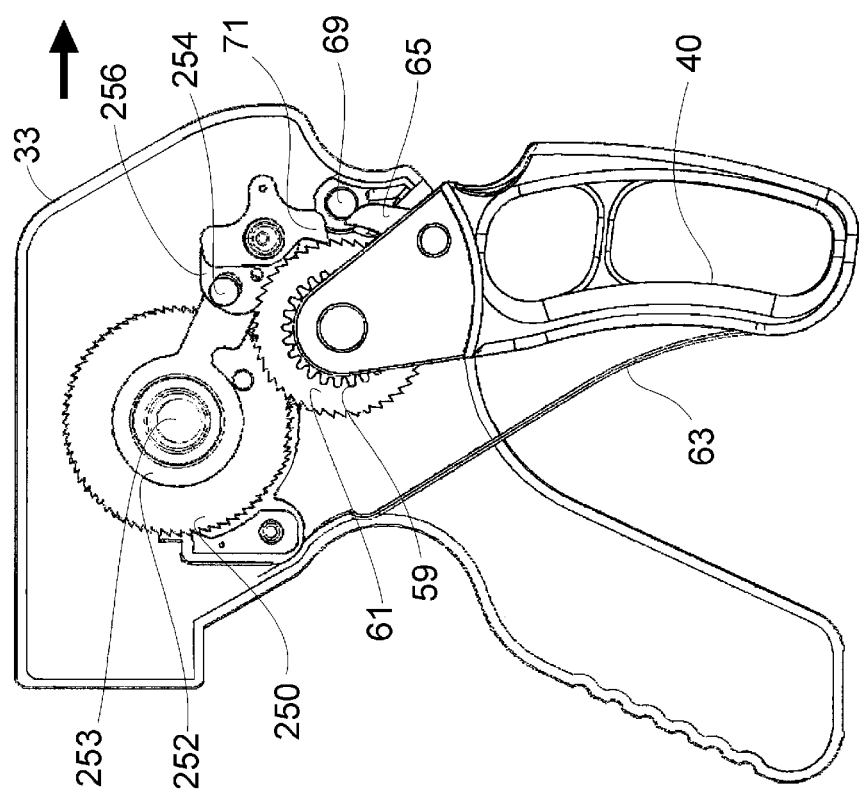
FIG. 9 illustrates a side view of the grip portion of the device of Example 1 of the present invention, with part of the housing on the front side of the drawing removed together with the rod-like member, the tension adjustment knob and parts associated to this, and the central gear (including the rotary drum which is in a body with the gear). The arrowhead in the figure indicates the direction of the tip of the device.

FIG. 9 illustrates a side view of the device of Example 1 of the present invention, with part of the housing on the front side of the drawing removed together with the rod-like member 34, a tension-adjusting knob 75 and parts associated to it, and the gear 57 which is united into a body with the rotary drum. In the figure, the arrowhead indicates the direction of the tip of the device. In the figure, a plate 252 is placed in front of a ratchet wheel 250, and the plate 252 is attached on one side of it to the same shaft 253 as the ratchet wheel is, pivotally within a predetermined range, and on the other side of it pivotally to another plate 256 by a pin 254.

Figure 10:
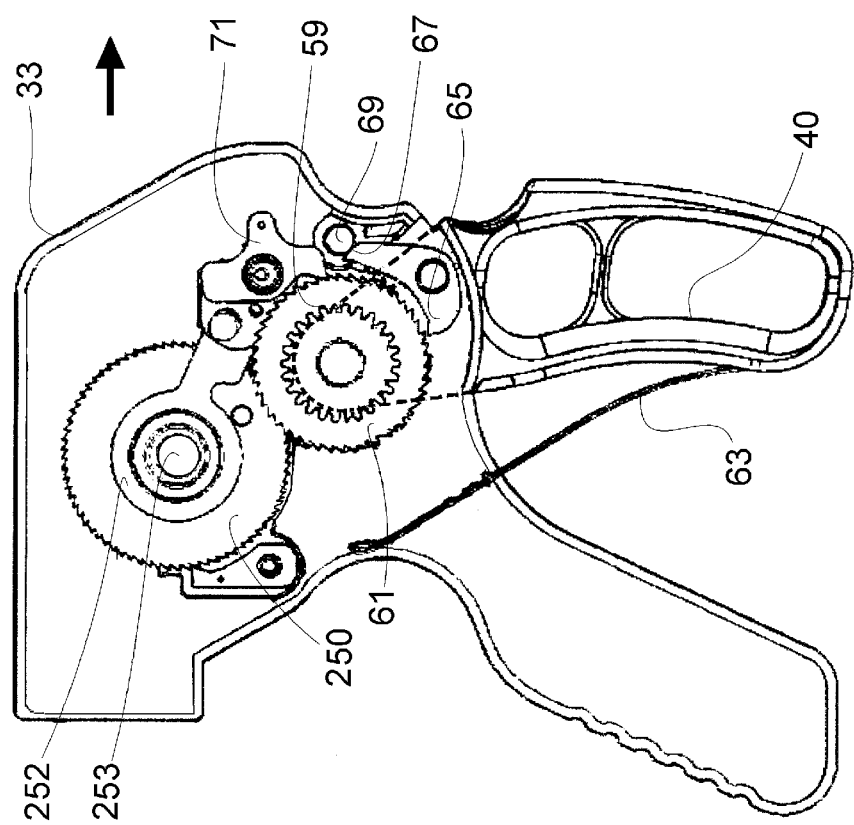
FIG. 10 illustrates a side view of the device of Example 1 of the present invention, in the state shown in FIG. 9, with the operation lever being partly made transparent to show the feed pawl located on the back side of the operation lever within the grip portion. The arrowhead in the figure indicates the direction of the tip of the device.

FIG. 10 illustrates a side view of the device of Example 1 of the present invention, in the state shown in FIG. 9, with the operation lever being partly made transparent to show the components located behind the part of operation lever within the grip portion. In the figure, on the backside of the operation lever 40, a feed pawl 65 is pivotally attached to a shaft which is provided on the operation lever 40, with a tip of the feed pawl being biased toward the ratchet wheel 61. The other end 67 of the feed pawl 65 is placed in contact with a pin 69 which is secured on the housing of the grip portion 33 to form a cam mechanism, so that when the operation lever 40 is at its forward position (i.e., where the operation lever is not pulled), the feed pawl 65, having pivoted anticlockwise in the figure, is off from the ratchet wheel 61. Further, the ratchet wheel 61 is engaged by a one-way detent 71 which is biased by a spring.

Figure 11:
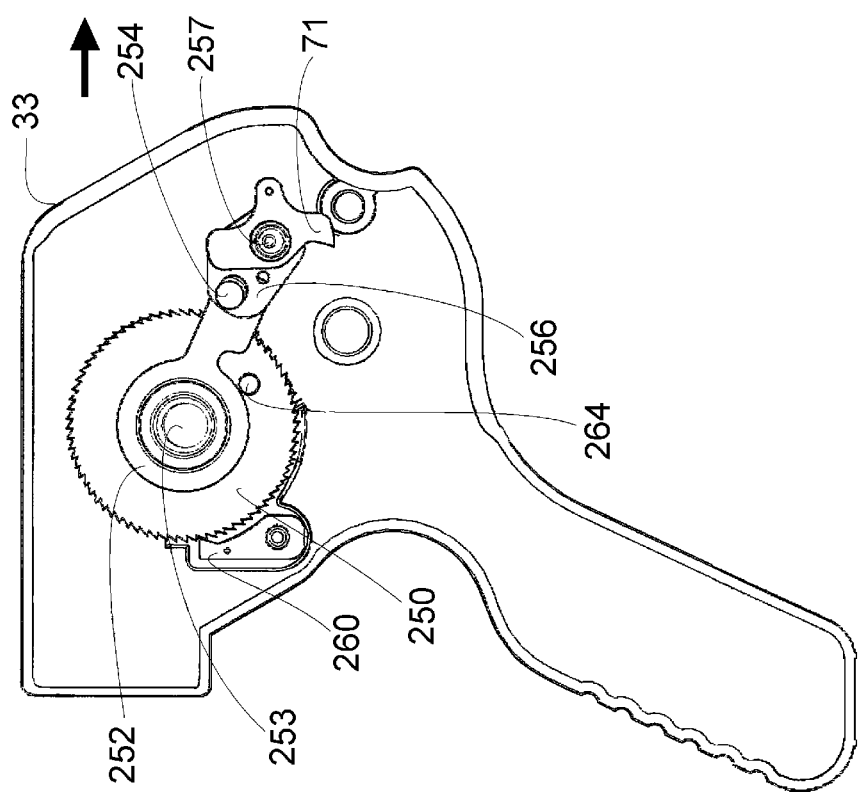
FIG. 11 illustrates a side view of the device of Example 1 of the present invention, with the operation lever (and the feed pawl) being removed together with the gear and the ratchet wheel coaxial with the operation lever, from the state shown in FIG. 10. The arrowhead in the figure indicates the direction of the tip of the device.

FIG. 11 illustrates a side view of the device of Example 1 of the present invention, with the operation lever being removed together with the gear 59, ratchet wheel 61, and feed pawl 65 attached thereto, from the state shown in FIG. 10. In the figure, the arrowhead indicates the direction of the tip of the device. In the figure, the one-way detent 71 for the ratchet wheel 61 (which is removed) is united with the shaft 257 of a release lever 73 which is mounted on the outside of the grip portion 33 (backside of the drawing), and, therefore, when the release lever 73 is pressed down (pivoted anticlockwise in the figure), the one-way detent is pivoted anticlockwise about the shaft 257, which causes its tip to disengage from the ratchet wheel 61 to allow a reverse rotation of the ratchet wheel 61, and therefore, of the gears 59 and 57 and the rotary drum, thus releasing the pull.

The ratchet wheel 250, thought attached to the same shaft 253 as is the gear 57 (and the rotary drum united with it), which is removed from the figure, is independent from the motion of the gear 57, and can rotate only clockwise in the figure. In the figure, indicated with the reference number 260 is a one-way detent for the ratchet wheel 250.

Likewise, the plate 256 is united with the pivotal shaft 257 for the releasing lever 73, and when the latter is pressed down (pivoted anticlockwise in the figure), the plate 256 also is pivoted in the same direction. As the pin 254 also shifts downward simultaneously in the figure, the plate 252 instead pivots clockwise about the shaft 253. This motion is reversible, and when the release lever 73 (which is biased toward the original position) is freed from the hand to let it return to the original position, the plates 252 and 256 both return to their respective original positions. In the figure, indicated with the reference number 264 is a projection acting as stopper, which, when the device is about to be used for the first time, is nested in the part of the plate 252 where its contour is indented.

Figure 12:
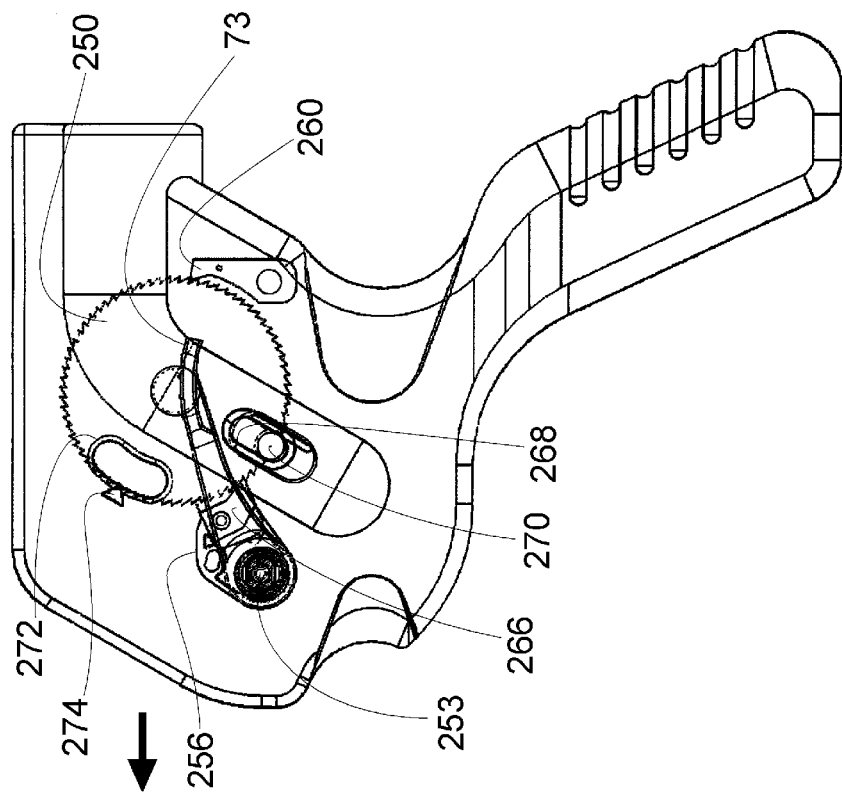
FIG. 12 illustrates a side view of the device of Example 1 of the present invention, seen from the same side as in FIG. 2, with some part being made transparent. The arrowhead in the figure indicates the direction of the tip of the device.

FIG. 12 illustrates a side view seen from the same side as in FIG. 2, with some part being made transparent, showing mechanical association between the release lever 73 and a release locking means in the grip portion. In the figure, the ratchet wheel 250 is engaged by a feed pawl 266, which is journaled on a plate secured to the release lever. Therefore, when the release lever 73 is pressed down, the feed pawl 266 pushes the ratchet wheel 250 to advance it stepwise in the anticlockwise direction in the figure (in the clockwise direction in FIG. 11). Thus, the ratchet wheel 250 is advanced, together with the projection 264 (FIG. 11), by a predetermined angle each time the release lever 73 is operated. As the release lever 73 is operated once at the end of each use of the device (i.e., a tying operation with a string of bone-tying cable by the device), the number of times the device has been used is equal to the number of times the projection 264 has been advanced. Thus, just after the device has been used a predetermined number of times (50 times in this example, though the number may be set as desired in accordance with its durability), the projection 264 has turned almost full circle along with the ratchet wheel 250 and abuts on the plate 252 again, on its backside this time. Starting in this state, when the device is used to pull the two arms of a bone-tying cable and then the release lever 73 is pressed down, the ratchet wheel 250 also is advanced clockwise along with the projection 264 in FIG. 11 at the same time as the plate 252 turns clockwise about the shaft 253. The projection 264 is secured to the ratchet wheel 250 and cannot turn back. Thus, the plate 252 is prevented by the projection 264 that is positioned on its backside from returning to its original position, and consequently, the release lever 73, plate 252, pin 254, and plate 256 can no longer return to their respective original positions, even after the release lever 73 is freed from the hand, and therefore the one-way detent 71 is kept disengaged with the ratchet wheel 61. Thus, the ratchet wheel 61 now is allowed to freely rotate in the reverse direction, which makes it impossible to pull the sliding block even by repeated pulling of the operation lever, and thus the device can no longer be used.

In FIG. 12, the grip portion 33 of the device is provided, on the same side of the release lever 73, with a locking means to prevent inadvertent pressing down of the release lever 73. In the present example, the locking means consists of a projection 270 which can be slid within a slot 268 to switch its position between the locking position and the releasing position, and is configured in such a fashion that the projection 270 can be held at either of the positions by respective juts provided within the slot, and that the position of the projection 270 can be switched beyond the juts by pushing the projection with a hand with a force above a certain level. Besides, in FIG. 12, the grip portion 33 in provided with a window 272, through which the scale marks (not shown) on the ratchet wheel which index the number of times the devices has been used (or the number of times left for use) can be read at the position indicated by a pointer 274.

Figure 13:
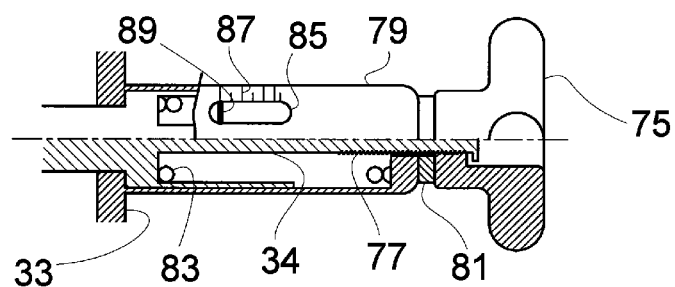
FIG. 13 is a schematic diagram showing the structure of the tension-adjusting mechanism of the device of Example 1 of the present invention.

FIG. 13 is a schematic diagram showing the structure of a tension-adjusting mechanism used for adjusting the tension of the bone-tying cable to a desired value as bones are firmly tied by the cable. In the figure, "75" indicates a tension-adjusting knob. The tension-adjusting knob 75 is provided with a female screw, which engages a male screw 77 formed at the rear end of the rod-like member 34. The rear end of the rod-like member 34 fits, slidably in the longitudinal direction, in a cylindrical member 79 which is combined into one body with the housing of the grip portion 33, and the tension-adjusting knob 75 abuts, with an intervening spacer 81 having a low coefficient of sliding friction, on the rear end of the cylindrical member 79. A coil spring 83 is enclosed between the rear end of the rod-like member 34 and the inner surface of the rear wall of the cylindrical member 79. When the tension-adjusting knob 75 is rotated clockwise, the rear end of the rod-like member 34, which is in screw-engagement with the knob, is drawn backward and retreat corresponding to the amount of rotation, thereby compressing the coil spring 83. Therefore, the more the amount of rotation of the tension-adjusting knob 75 is, the more compressed the coil spring 83 becomes, and the greater accumulation of repulsive force accumulates in the spring. The cylindrical member 79 is provided with a window 85, and around the edges of the window 85 are provided scale marks 87 which correspond to the strength of the tension. A bar 89, which is seen through the window 85 of the cylindrical member 79, is marked near the rear end of the rod-like member 34.

Figure 14:
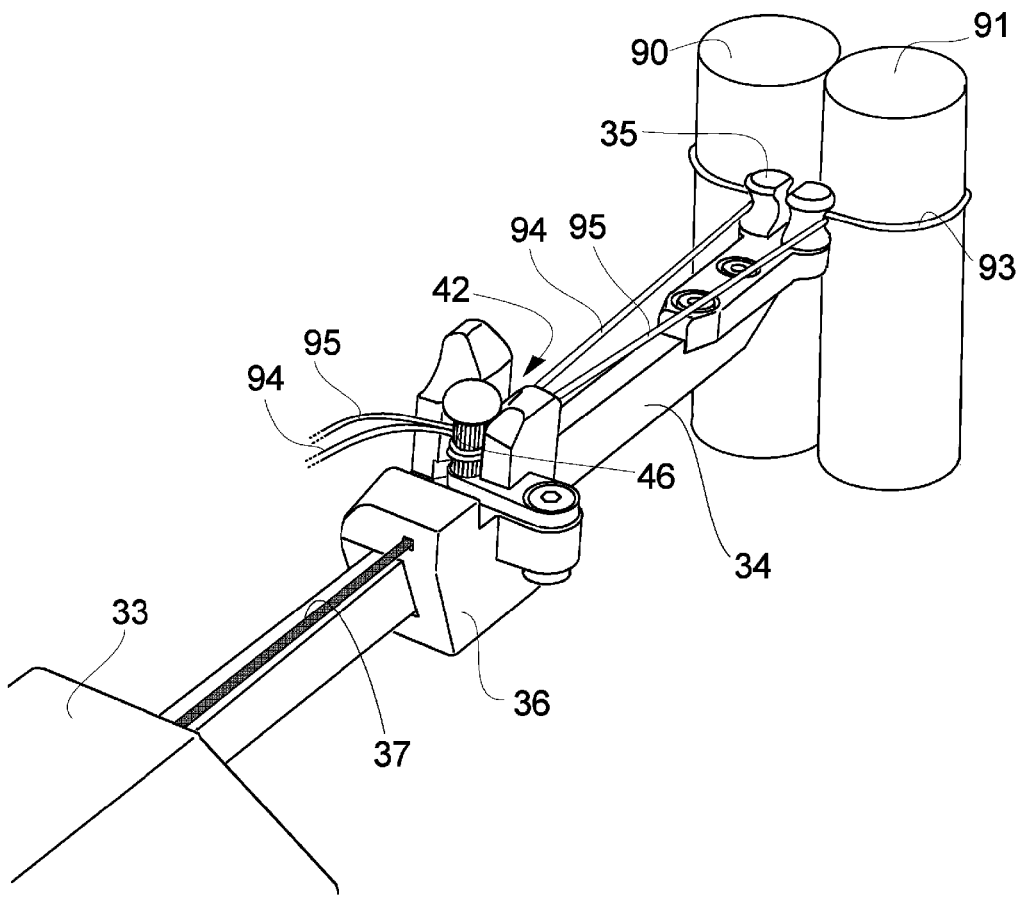
FIG. 14 illustrates an enlarged partial view of the device of Example 1 of the present invention, seen obliquely from behind, as bones are being tied firmly by it.

FIG. 14 is an enlarged partial view of the device of this example seen obliquely from behind as two bones are being firmly tied by it. In the figure, "93" indicates a loop of a bone-tying cable, with which the bones 90, 91 are being fastened, and "94" and "95" indicate two arms extending from a provisional knot (not seen behind the knot-supporting means 35) of the bone-tying cable. The procedure up to the formation of a provisional knot is the same as has been described with reference to FIGS. 1 and 3 as for a conventional device. The two arms 94, 95 of the bone-tying cable are separated away from each other, rightward and leftward, respectively, relative to the knot-supporting means 35, then are pulled backward, with the provisional knot being supported by the knot-supporting means 35, and the both arms are passed through the through groove 42 as a bundle. Then they are wound once about the locking member 46, and the operation lever 40 is pulled a few times to make the sliding block 36 retreat. As a result, the two arms 94, 95 of the bone-tying cable becomes tense between the locking member 46 and the knot-supporting means 35, and the locking member 46 about which they are wound is forced to fit in the rocking recess 44. While the operation lever 40 is repeatedly pulled following this situation, causing the sliding block 36 to further retreat, the tension of the two arms 94, 95 of the bone-tying cable is elevated between the locking member 46 and the knot-supporting means 35, which makes the locking member 46 tightly fit in the V-shaped locking recess 44, clamping with greater force the two arms 94, 95 of the bone-tying cable between it and the locking recess 44. Thus, as a result of increasing frictional force between them, the two arms 94, 95 of the bone-tying cable are tightly secured in place. Besides, instead of separating the two arms 94, 95 of the bone-tying cable to both sides of the knot-supporting means 35, it is also allowed to pull them backward through the slit defined in the knot-supporting means 35.

As further repeated pulling of the operation lever 40 causes further retreat of the sliding block 36, thereby increasing the tension of the two arms 94, 95 of the cable, the cable mutually slips between its contact surfaces within the provisional knot. This makes the loop 93 shrink in its size and gradually and firmly tie the bones 90, 91 at increasing strength. Throughout this process, though the rod-like member 34 also is pulled backward at the knot-supporting means 35 by the pull cable via the locking member 46 and the sliding block 36, it continues to stay at its original position, since it is biased forward at its rear end by the coil spring 83, as far as the strength of this bias is not overcome by the backward pull.

Figure 15:
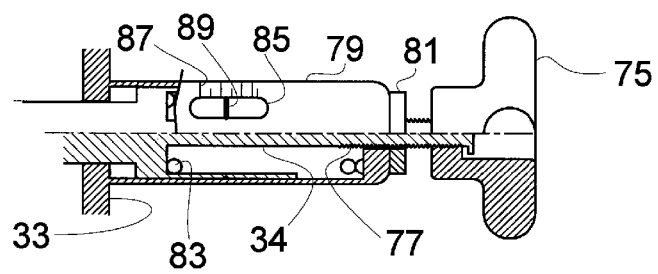
FIG. 15 is a schematic diagram showing the action of the tension-adjusting mechanism.

Referring to FIG. 15, at the moment when the tension of the loop 93, which is fastening the bones 90, 91, reaches a desired strength, and the pulling force just slightly exceeds the predetermined value which is related to that strength, the rod-like member 34 slightly retreats backward. This retreat can be detected either as a retreat of the tension-adjusting knob 75 or as a shift of the bar 89 seen through the window 85 of the cylindrical member 79. Therefore, the surgeon can know that the predetermined strength of tension has just been achieved, at the moment when the rod-like member 34 shifted slightly backward from its original position.

Thus, after the predetermined tension has been achieved, the release lever 73 is pulled down to disengage the one-way detent 71 from the teeth of the ratchet wheel, thereby releasing the ratchet mechanism. Thus, as the sliding block 36 is released from the backward pull, the locking member 46 also is released from its engagement with the locking recess 44, and the two arms of the bone-tying cable therefore can be removed from the locking member 46. The process using the device now has been finished, and then the knot is fixed, as is done conventionally, by additional knots or an adhesive, or the like, so that it may not be displaced.

Except the gears, ratchets and pawls, each of which especially receives a concentrated load, the components of device of the present invention (e.g., the grip portion) are made of plastics (e.g., engineering plastics such as polyether ether ketones).

Figure 16:
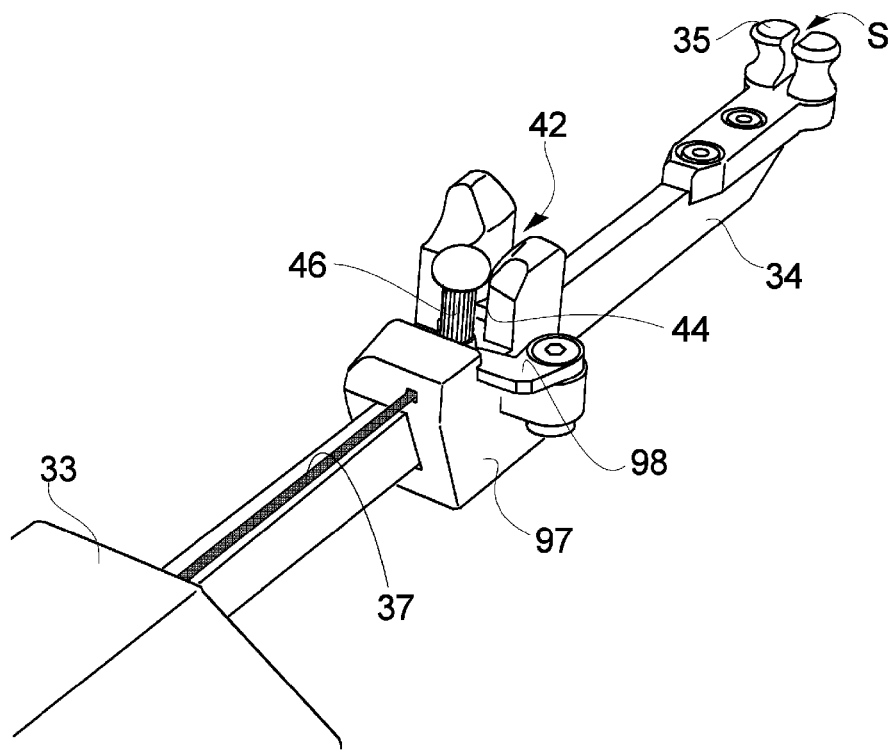
FIG. 16 illustrates an enlarged partial view of the bone-tying cable tightening device of Example 2 of the present invention, seen obliquely from behind.

FIG. 16 illustrates an enlarged partial view of another example of the present invention, seen obliquely from behind. In the figure, the same reference numbers as those appear in Example 1 correspond to those parts in Example 1, respectively. In this example, the arm 98 installed pivotably on the sliding block 97 is formed in a shape of a hook, and owing to its contour defined as receding on its inner side, interference of the arm 98 with the edge of the locking recess 44 is avoided when the arm pivots forward. Other structures, functions and manners of handling of this example are as described for Example 1.

Example 3

Figure 17:
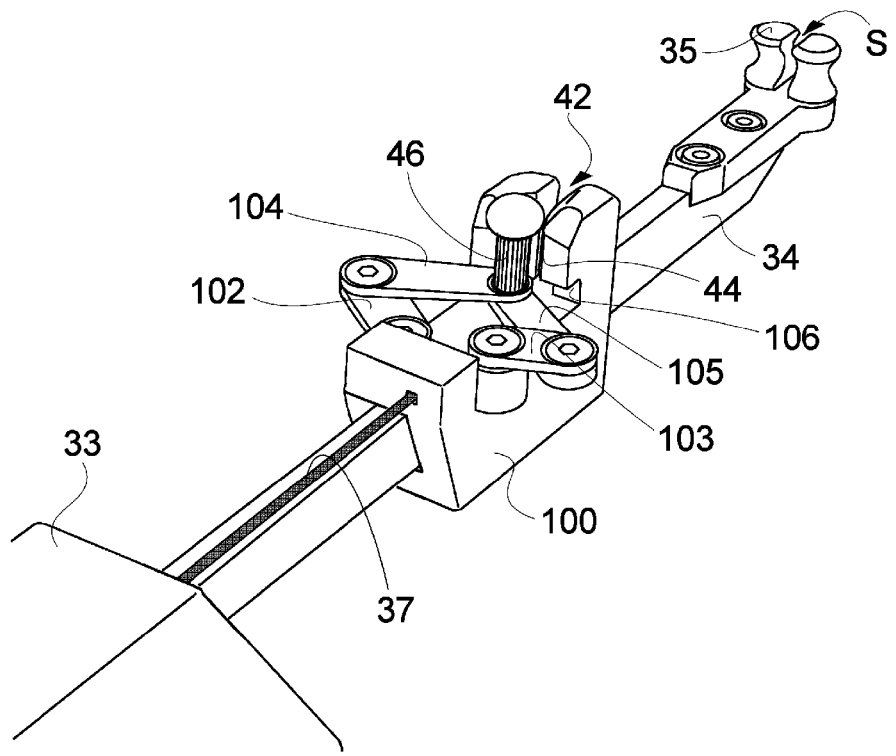
FIG. 17 illustrates an enlarged partial view of the bone-tying cable tightening device of Example 3 of the present invention, seen obliquely from behind.

FIG. 17 illustrates an enlarged partial view of still another example of the present invention, seen obliquely from behind. In the figure, the same reference numbers as those appear in Example 1 correspond to those parts in Example 1, respectively. In this example, the sliding block 100 is provided with a pair of first arms 102, 103 which pivotably extend diagonally in lateral directions from both lateral sides of the sliding block, as well as with a pair of second arms 104, 105 pivotably extending diagonally in inward directions from the respective tips of the first arms. And the second arms 104, 105 are connected at their tips pivotably with each other. Thus, a five-link chain is formed consisting of the sliding block 100, the pair of the first arms 102, 103, and the pair of the second arms 104, 105. At the tips of the pair of the second arms is fixed a locking member 46. The pair of first arms 102, 103 are journaled on the sliding block 100 and biased in rearward pivoting directions, respectively, by springs installed around their pivotal axes. In order to avoid interference that could happen when the second arms 104, 105 move forward, the sliding block 100 defines indentations 106 in the edges of the locking recess 44. Thus, the locking member 46, which usually rests rearward away from the locking recess 44, can advance in a linear fashion to fit in the locking recess 44 when a forward external force is applied to it. Other structures, functions and manners of handling of this example are as described for Example 1.

Example 4

Figure 18:
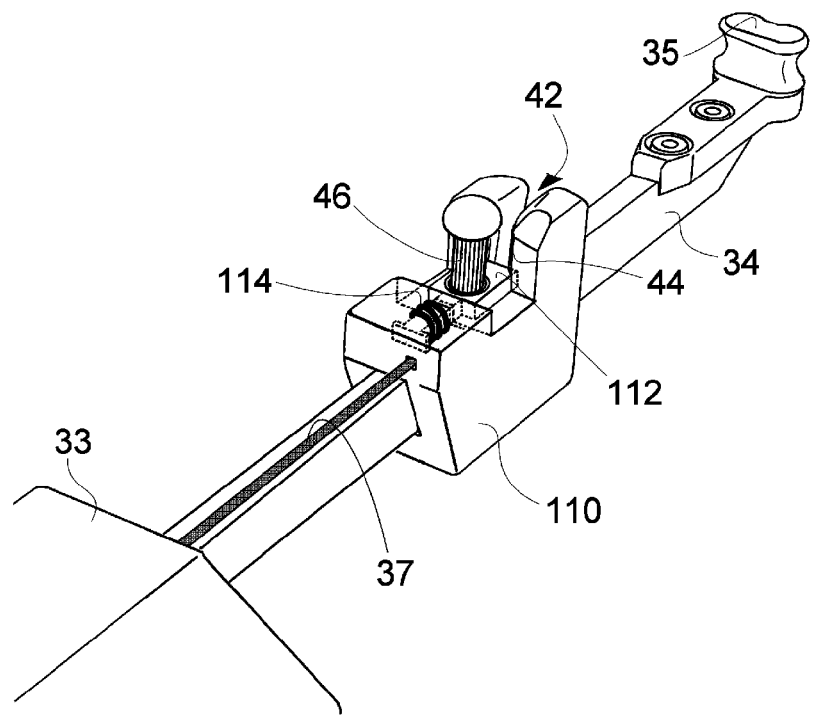
FIG. 18 illustrates an enlarged partial view of the bone-tying cable tightening device of Example 4 of the present invention, seen obliquely from behind.

FIG. 18 illustrates an enlarged partial view of still another example of the present invention, seen obliquely from behind. In the figure, the same reference numbers as those appear in Example 1 correspond to those parts in Example 1, respectively. In this example, the sliding block 110 has a basal plate 112, which is mounted on it slidably in the longitudinal direction and is biased backward by a coil spring 114 confined in the rear of it, and the locking member 46 is fixed on the basal plate 112. Thus, the locking member 46, which usually rests rearward away from the locking recess 44, can advance in a linear fashion to fit in the locking recess 44 when a forward external force is applied to it. Other structures, functions and manners of handling of this example are as described for Example 1. Besides, in this example, the knot-supporting means 35 is of a single-body structure, instead of those shown in Examples 2, 3.

Example 5

Figure 19:
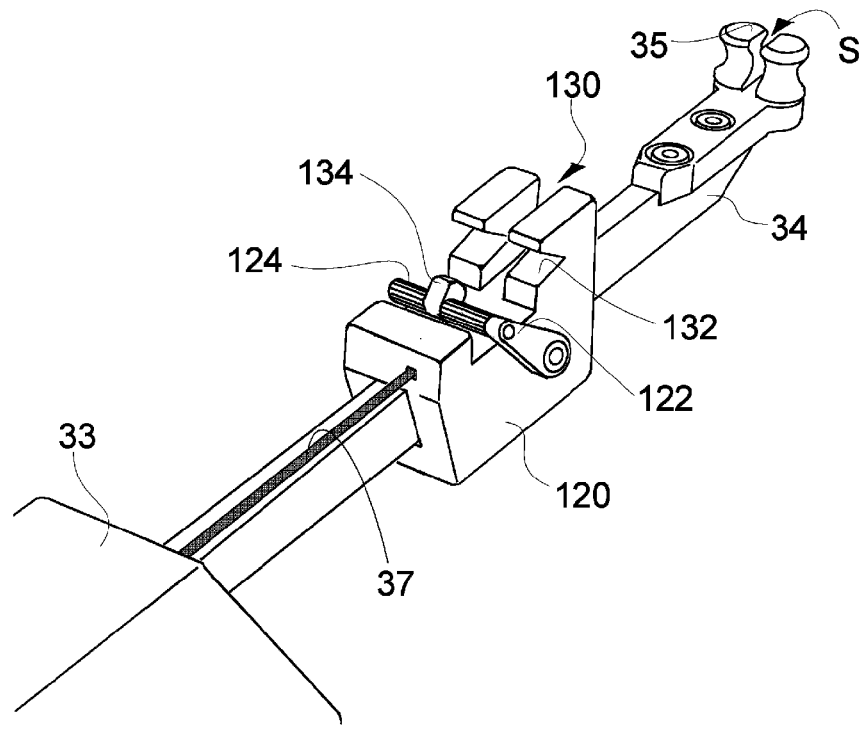
FIG. 19 illustrates an enlarged partial view of the bone-tying cable tightening device of Example 5 of the present invention, seen obliquely from behind.

FIG. 19 illustrates an enlarged partial view of still another example of the present invention, seen obliquely from behind. In the figure, the same reference numbers as those seen in Example 1 correspond to those parts in Example 1, respectively. In this example, an arm 122 is pivotably attached to the sliding block 120 on one of its lateral sides and extends generally upward while slanting backward, and at the tip of the arm is fixed a locking member 124 which extends inward over the sliding block 120. The arm 122 is biased backward by a spring inside the sliding block 120. A through groove 130 is defined in the sliding block 120, and a locking recess 132 having a V-shaped cross section extends transversing the rear end of the through groove, intersecting the cross section of it. Thus, the locking member 124, which usually rests rearward away from the locking recess 132, can advance to fit in the locking recess 132 when a forward external force is applied to it. The projection 134 provided at the center of the locking member 124 is a structure for preventing the two arms of the bone-tying cable from being wound exclusively right above the through groove 130, and it is of a width which allows itself to just fit in the through groove 130. Other structures, functions and manners of handling of this example are as described for Example 1.

Example 6

Figure 20:
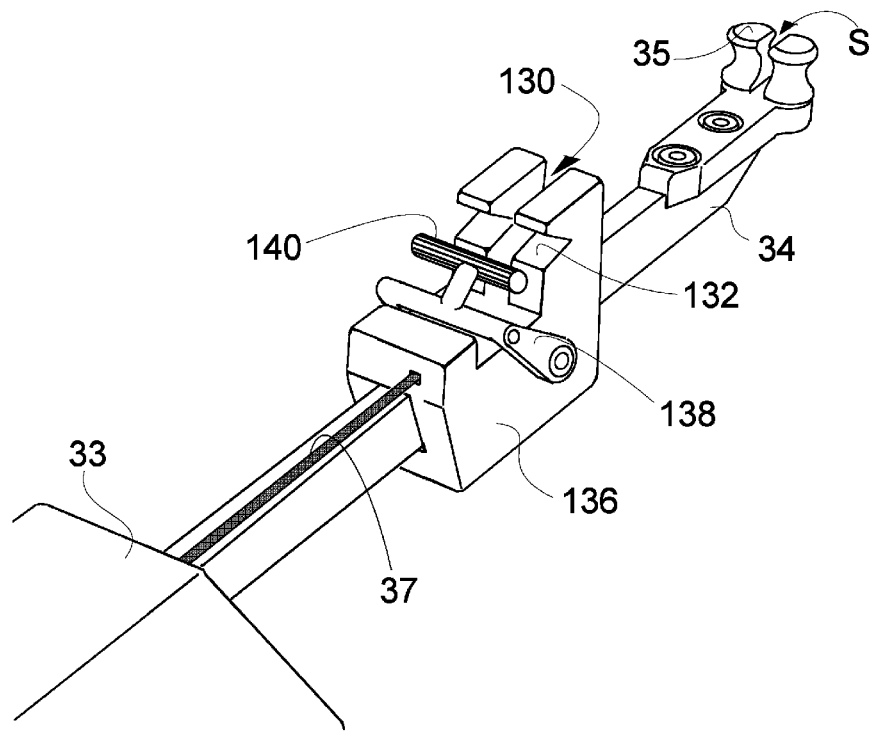
FIG. 20 illustrates an enlarged partial view of the bone-tying cable tightening device of Example 6 of the present invention, seen obliquely from behind.

FIG. 20 illustrates an enlarged partial view of still another example of the present invention, seen obliquely from behind. In the figure, the same reference numbers as those seen in Example 1 correspond to those parts in Example 1, respectively. In this example, arms 138 which are pivotably attached to the sliding block 136 on its both lateral sides extend generally upward while slanting backward, and then, after extending inward above the sliding block to unite into one body in the middle, further extends generally upward while slanting forward, and at the tip of the arm thus formed is attached a locking member 140. The arms 138 are biased backward by a spring inside the sliding block 136. A through groove 130 is defined in the sliding block 136, and a locking recess 132 having a V-shaped cross section extends transversing the rear end of the through groove, intersecting the cross section of it. Thus, the locking member 140, which usually rests rearward away from the locking recess 132, can advance to fit in the locking recess 132 when a forward external force is applied to it. Other structures, functions and manners of handling of this example are as described for Example 1.

Example 7

Figure 21:
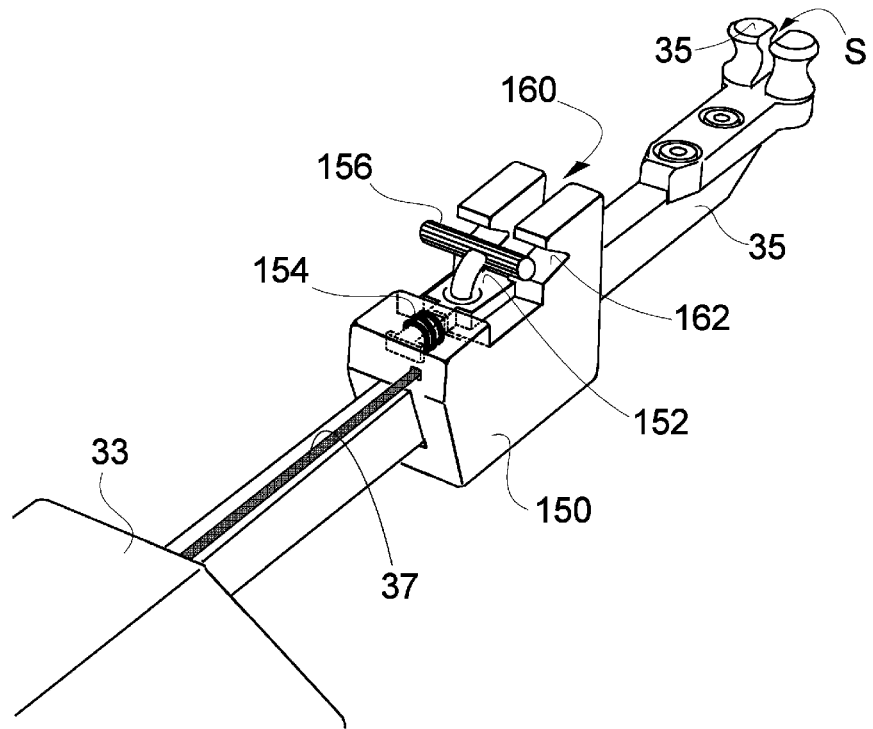
FIG. 21 illustrates an enlarged partial view of the bone-tying cable tightening device of Example 7 of the present invention, seen obliquely from behind.

FIG. 21 illustrates an enlarged partial view of a still another example of the present invention, seen obliquely from behind. In the figure, the same reference numbers as those seen in Example 1 correspond to those parts in Example 1, respectively. In this example, the sliding block 150 has a basal plate 152, which is mounted on it slidably in the longitudinal direction and is biased backward by a coil spring 154 confined in the rear of it, and the locking member 156 is fixed on the basal plate 152. A through groove 160 is defined in the sliding block 150, and a locking recess 162 having a V-shaped cross section extends transversing the rear end of the through groove, intersecting the cross section of it. Thus, the locking member 156, which usually rests rearward away from the locking recess 162, can advance in a linear fashion to fit in the locking recess 162 when a forward external force is applied to it. Other structures, functions and manners of handling of this example are as described for Example 1.

Example 8

Figure 22:
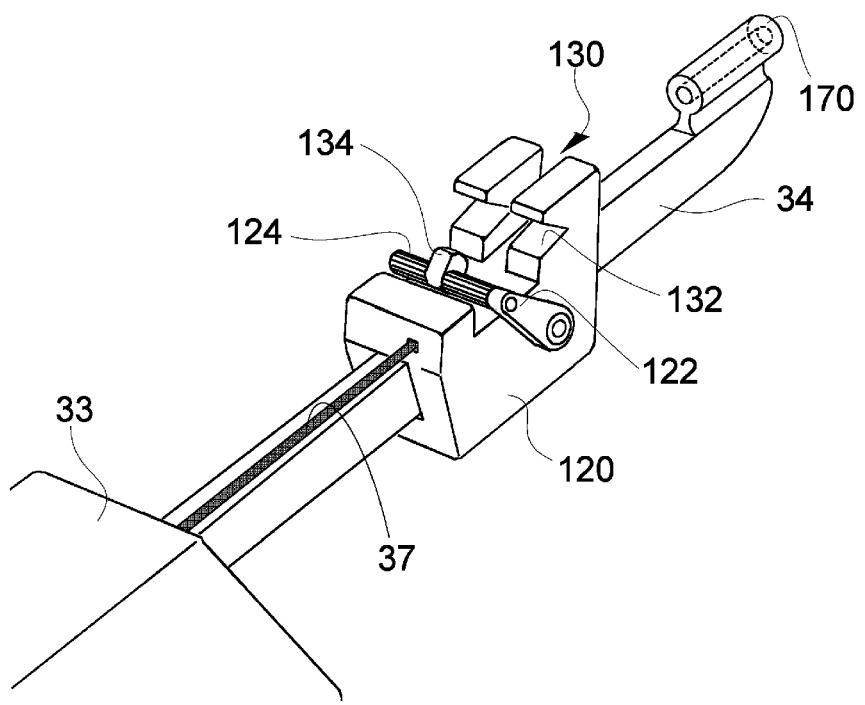
FIG. 22 illustrates an enlarged partial view of the bone-tying cable tightening device of Example 8 of the present invention, seen obliquely from behind.

FIG. 22 illustrates an enlarged partial view of still another example of the present invention, seen obliquely from behind. The present example is the same as Example 5, except that it is provided with a cylindrical portion 170 instead of the knot-supporting means 35. The cylindrical portion 170 is used to support at its tip the provisional knot, with the two arm of the cable being passed through its bore. In order to pass two arms of a bone-tying cable through the bore, such a cable may be chosen as having at either end a structure (e.g., a loop of a string) to which a wire can be hooked, and the cable then is passed using a wire which is hooked to the structures as a guide.

INDUSTRIAL APPLICABILITY

As it is of a structure that does not allow itself to be used beyond a predetermined number of times, the bone-tying cable tightening device of the present invention can be constructed using plastics for most of its components, and therefore can be provided as a much lighter and less costly device than the conventional ones. And as it guarantees itself to be disposed of after having been used a predetermined number of times, it does not need maintenance as is necessary with conventional devices, but entails no costs for maintenance. Further, as it is disposed of, an effect of mass production can work to further reduce its production cost.

REFERENCE NUMBERS LIST

33=grip portion
34=rod-like member
35=knot-supporting means
36=sliding block
37=pull cable
40=operation lever
42=through groove
44=locking recess
46=locking member
48=arm
50=indentation
57=gear
59=gear
61=ratchet wheel
63=leaf spring
65=feed pawl
67=other end of feed pawl
69=pin
71=one-way detent
73=release lever
75=tension-adjusting knob
79=cylindrical member
81=spacer
83=coil spring
85=window
87=scale marks
90=bone
91=bone
93=loop of bone-tying cable
94=arm of bone-tying cable
95=arm of bone-tying cable
100=sliding block
102=first arm
103=first arm
104=second arm
105=second arm
106=indentation
110=sliding block
112=basal plate
114=coil spring
120=sliding block
122=arm
124=locking member
130=through groove
132=locking recess 134=projection
136=sliding block
138=arm
140=locking member
150=sliding block
152=basal plate
154=coil spring
156=locking member
160=through groove
162=locking recess
170=cylindrical portion
250=ratchet wheel
252=plate
253=shaft
254=pin
256=plate
257=shaft
260=one-way detent
264=stopper
266=feed pawl
268=slot
270=projection
272=window
274=pointer
B=through bore
S=slit

The invention claimed is:

1. A bone-tying cable tightening device for firmly tying up objects to be tied, by pulling two arms which extend from a knot of a cable which ties the objects to be tied, comprising
a grip portion to be held with a hand,
a rod-like member which extends forward from the grip portion,
a knot supporter provided at a tip of the rod-like member to support the knot when the two arms are pulled,
a sliding block mounted around the rod-like member in a longitudinally slidable fashion, which sliding block is provided with a cable holder to grip and hold the two arms together,
a pulling mechanism installed in the grip portion to pull the sliding block, wherein said pulling mechanism is connected to the sliding block via a tension transmitter,
an operation lever provided in the grip portion to drive the pulling mechanism, wherein
the knot supporter is of a structure which defines, above the rod-like member,
(1) supporting faces on both sides thereof on which the two arms can be hooked away from each other and laterally relative to the longitudinal axis of the rod-like member, and/or
(2) a slit or bore through which the two arms can be passed, and
wherein
the cable holder provided to the sliding block comprises
(a) a longitudinal through groove defined in an upper part of the sliding block,
(b) a locking recess which extends at a rear end of the through groove, either transversing the cross section of the through groove or containing the cross section of the through groove along the central axis thereof, and whose width, in the cross section thereof, widens in the rearward direction,
(c) a backward biased locking member about which the two arms are to be wound, and which is provided movably back and forth behind the locking recess on the upper side of the sliding block and is so made that the forward movement thereof is blocked when it proceeds in the locking recess and abuts, with the side faces thereof, on the same, and
wherein,
the pulling mechanism includes a one-way detent which acts to prevent returning of the pulling mechanism from the position to which the pulling mechanism has been driven to the position at which the pulling mechanism rested before being driven,
the device is provided with a pull releaser which releases the one-way detent to allow the pulling mechanism to return from the position up to which the pulling mechanism has been driven to the position at which the pulling mechanism rests before driven, which pull-releasing mechanism is so configured as to allow a releasing operation from outside of the device, and
wherein the device is provided with a locking release which locks the one-way detent in a released state once the pull releaser has been operated the predetermined number of times.

2. The bone-tying cable tightening device according to claim 1, wherein the locking release is advanced stepwise, by each operation of the pull releaser, from a predetermined initial position at which the locking release does not prevent the action of the one-way detent toward a predetermined final position at which the locking release locks the one-way detent in a released state, and wherein the locking release is so configured as to reach the predetermined final position and lock the one-way detent in the released state after the pull releaser has been operated the predetermined number of times.

3. The device according to claim 1, wherein the pulling mechanism includes a first ratchet wheel which is advanced stepwise in one direction by the operation of the operation lever, wherein the one-way detent is a one-way detent which engages the first ratchet wheel.

4. The device according to claim 1, wherein the locking release includes a second ratchet wheel which is advanced stepwise in one direction by the operation of the pull releaser and a stopper which is advanced toward the final position by the advance of the second ratchet wheel, wherein the stopper is so configured as to abut, at the final position, on the one-way detent or a member which is interlocked therewith to prevent the motion thereof, and thereby to lock the one-way detent in a released state.

5. A bone-tying cable tightening device for firmly tying up objects to be tied, by pulling two arms which extend from a knot of a cable which ties the objects to be tied, comprising
a grip portion to be held with a hand,
a rod-like member which extends forward from the grip portion,
a knot-supporting means provided at a tip of the rod-like member to support the knot when the two arms are pulled,
a sliding block mounted around the rod-like member in a longitudinally slidable fashion, which sliding block is provided with a cable-holding means to grip and hold the two arms together,
a pulling means installed in the grip portion to pull the sliding block, which pulling means is connected to the sliding block via a tension transmitter means,
an operation lever provided in the grip portion to drive the pulling means, wherein the knot-supporting means is of a structure which defines, above the rod-like member,
(1) supporting faces on both sides thereof on which the two arms can be hooked away from each other and laterally relative to the longitudinal axis of the rod-like member, and/or
(2) a slit or bore through which the two arms can be passed, and
wherein
the cable-holding means provided to the sliding block comprises
(a) a longitudinal through groove defined in an upper part of the sliding block,
(b) a locking recess which extends at a rear end of the through groove, either transversing the cross section of the through groove or containing the cross section of the through groove along the central axis thereof, and whose width, in the cross section thereof, widens in the rearward direction,
(c) a backward biased locking member about which the two arms are to be wound, and which is provided movably back and forth behind the locking recess on the upper side of the sliding block and is so made that the forward movement thereof is blocked when it proceeds in the locking recess and abuts, with the side faces thereof, on the same, and
wherein,
the pulling means includes a one-way detent means which acts to prevent returning of the pulling means from the position to which the pulling means has been driven to the position at which the pulling means rested before being driven,
the device is provided with a pull-releasing means which releases the one-way detent means to allow the pulling means to return from the position up to which the pulling means has been driven to the position at which the pulling means rests before driven, which pull-releasing means is so configured as to allow a releasing operation from outside of the device, and
wherein the device is provided with a release locking means which locks the one-way detent means in a released state once the pull-releasing means has been operated the predetermined number of times.

6. The bone-tying cable tightening device according to claim 5, wherein the release locking means is advanced stepwise, by each operation of the pull-releasing means, from a predetermined initial position at which the release locking means does not prevent the action of the one-way detent means toward a predetermined final position at which the release locking means locks the one-way detent means in a released state, and wherein the release locking means is so configured as to reach the predetermined final position and lock the one-way detent means in the released state after the pull-releasing means has been operated the predetermined number of times.

7. The device according to claim 5, wherein the pulling means includes a first ratchet wheel which is advanced stepwise in one direction by the operation of the operation lever, wherein the one-way detent means is a one-way detent which engages the first ratchet wheel.

8. The device according to claim 5, wherein the release locking means includes a second ratchet wheel which is advanced stepwise in one direction by the operation of the pull-releasing means and a stopper which is advanced toward the final position by the advance of the second ratchet wheel, wherein the stopper is so configured as to abut, at the final position, on the one-way detent means or a member which is interlocked therewith to prevent the motion thereof, and thereby to lock the one-way detent means in a released state.

* * * * *